US007262199B2

(12) United States Patent
Fraley et al.

(10) Patent No.: US 7,262,199 B2
(45) Date of Patent: Aug. 28, 2007

(54) TYROSINE KINASE INHIBITORS

(75) Inventors: Mark E. Fraley, North Wales, PA (US); Scott R. Hambaugh, Philadelphia, PA (US); Robert S. Rubino, Williamsville, NY (US); Randall W. Hungate, Newbury Park, CA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/537,758

(22) PCT Filed: Dec. 5, 2003

(86) PCT No.: PCT/US03/38716

§ 371 (c)(1),
(2), (4) Date: Jun. 6, 2005

(87) PCT Pub. No.: WO2004/052286

PCT Pub. Date: Jun. 24, 2004

(65) Prior Publication Data

US 2006/0183755 A1   Aug. 17, 2006

Related U.S. Application Data

(60) Provisional application No. 60/432,453, filed on Dec. 11, 2002.

(51) Int. Cl.
  *C07D 487/04*  (2006.01)
  *C07D 413/04*  (2006.01)
  *A61K 31/519*  (2006.01)
  *A61K 31/535*  (2006.01)
  *A61P 35/00*   (2006.01)
  *A61P 3/08*    (2006.01)
  *A61P 19/02*   (2006.01)

(52) U.S. Cl. ................ 514/259.3; 514/231.5; 544/281; 544/111

(58) Field of Classification Search ........... 544/281, 544/111; 514/259.3, 231.5
See application file for complete search history.

(56) References Cited

U.S. PATENT DOCUMENTS 6,245,759 B1   6/2001  Bilodeau et al.
6,380,203 B1 * 4/2002  Bilodeau et al. ......... 514/259.3
6,544,988 B1 * 4/2003  Bilodeau et al. ......... 514/233.2

FOREIGN PATENT DOCUMENTS

WO   WO-00/53605 A1 * 9/2000

OTHER PUBLICATIONS

Hasan et al. Expert Opin. Biol. Ther. 1(4): 703-718, 2001.*
Pegram et al. Semin. Oncol. 29(3) Suppll11) 29-37, 2002.*
Cecil Textbook of Medicine, edited by Bennet, J.C., and Plum F., 20th edition, vol. 1, 1004-1010, 1996.*
Bruggen, N.V., et al., "VEGF antagonism reduces edema formation and tissue damage after ischemia/reperfusion injury in the mouse brain", The Journal of Clinical Investigation, vol. 104, pp. 1613-1620 (1999).
Deckers, M.M.L., .et al., "Expression of Vascular Endothelial Growth Factors and Their Receptors during Osteoblast Differentiation", Endocrinology, vol. 141, pp. 1667-1674 (2000).
Fraley, M. E., et al., "Optimization of a Pyrazolo [1,5-alpyrimidine Class of KDR Kinase Inhibitors: Improvements in Physical Properties Enhance Cellular Activity and Pharmacokinetics", Bioorganic & Medicinal Chemistry Letters, vol. 12, pp. 3537-3541 (2002).
Fraley, M.E., et al., "Property-Based Design of KDR Kinase Inhibitors", Current Medicinal Chemistry, vol. 11, pp. 709-719 (2004).
Fraley, M.E., et al., "Synthesis and Initial SAR Studies of 3,6-Disubstituted Pyrazolo [1,5-alpyrimidines: A New Class of KDR Kinase Inhibitors", Bioorganic & Medicinal Chemistry Letters, vol. 12, pp. 2767-2770, (2002).
Gerber, H.P., et al., "VEGF couples hypertrophic cartilage remodeling, ossification and angiogenesis during endochondral bone formation", Nature Medicine, vol. 5, pp. 623-628 (1999).
Greenberg, D.A., et al., "Angiogenesis and Stroke", Drug News Perspect, vol. 11, pp. 265-270 (1998).
Hasegawa, T., et al., "Intracortical osteoblastic osteosarcoma with oncogenic rickets", Skeletal Radiology, vol. 28, pp. 41-45 (1999).
Nakagawa, M., et al., "Vascular endothelial growth factor (VEGF) directly enhances osteoclastic bone resorption and survival of mature osteoclasts", FEBS Letters, vol. 473, pp. 161-164 (2000).
Paul, R. et al., "Src deficiency of blockade of Src activity in mice provides cerebral protection following stroke", Nature Medicine, vol. 7, pp. 222-227 (2001).
Rak, J., et a., "Mutant ras Oncogenes Upregulate VEGF/FPF Expression: Implications for Induction and Inhibition of Tumor Angiogenesis", Cancer Research, vol. 55, pp. 4575-4580 (1995).

* cited by examiner

*Primary Examiner*—Venkataraman Balasubramanian
(74) *Attorney, Agent, or Firm*—Nicole M. Beeler; David M. Muthard

(57) ABSTRACT

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, macular edema, retinal ischemia, inflammatory diseases, and the like in mammals.

8 Claims, No Drawings

TYROSINE KINASE INHIBITORS

PRIORITY CLAIM

This application is a §371 application of PCT/US03/38716 that was filed on Dec. 5, 2003, which claims priority from the U.S. Provisional Application No. 60/432,453, filed on Dec. 11, 2002, now expired.

BACKGROUND OF THE INVENTION

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

The following is provided as background information only and should not be taken as an admission that any subject matter discussed or that any reference mentioned is prior art to the instant invention.

Tyrosine kinases are a class of enzymes that catalyze the transfer of the terminal phosphate of adenosine triphosphate to tyrosine residues in protein substrates. Tyrosine kinases are believed, by way of substrate phosphorylation, to play critical roles in signal transduction for a number of cell functions. Though the exact mechanism of signal transduction is still unclear, tyrosine kinases have been shown to be important contributing factors in cell proliferation, carcinogenesis and cell differentiation.

Tyrosine kinases can be categorized as receptor type or non-receptor type. Receptor type tyrosine kinases have an extracellular, a transmembrane, and an intracellular portion, while non-receptor type tyrosine kinases are wholly intracellular.

The receptor-type tyrosine kinases are comprised of a large number of transmembrane receptors with diverse biological activity. In fact, about twenty different subfamilies of receptor-type tyrosine kinases have been identified. One tyrosine kinase subfamily, designated the HER subfamily, is comprised of EGFR, HER2, HER3, and HER4. Ligands of this subfamily of receptors include epithileal growth factor, TGF-α, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-α and β receptors, CSFIR, c-kit and FLK-II. Then there is the FLK family which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., DN&P 7(6):334-339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further subdivided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen Oncogene, 8:2025-2031 (1993), which is hereby incorporated by reference.

Both receptor-type and non-receptor type tyrosine kinases are implicated in cellular signaling pathways leading to numerous pathogenic conditions, including cancer, psoriasis and hyperimmune responses.

Several receptor-type tyrosine kinases, and the growth factors that bind thereto, have been suggested to play a role in angiogenesis, although some may promote angiogenesis indirectly (Mustonen and Alitalo, J. Cell Biol. 129:895-898, 1995). One such receptor-type tyrosine kinase is fetal liver kinase 1 or FLK-1. The human analog of FLK-1 is the kinase insert domain-containing receptor KDR, which is also known as vascular endothelial cell growth factor receptor 2 or VEGFR-2, since it binds VEGF with high affinity. Finally, the murine version of this receptor has also been called NYK (Oelrichs et al., Oncogene 8(1):11-15, 1993). VEGF and KDR are a ligand-receptor pair that play an important role in the proliferation of vascular endothelial cells, and the formation and sprouting of blood vessels, termed vasculogenesis and angiogenesis, respectively.

Angiogenesis is characterized by excessive activity of vascular endothelial growth factor (VEGF). VEGF is actually comprised of a family of ligands (Klagsburn and D'Amore, Cytokine & Growth Factor Reviews 7:259-270, 1996). VEGF binds the high affinity membrane-spanning tyrosine kinase receptor KDR and the related fms-like tyrosine kinase-1, also known as Flt-1 or vascular endothelial cell growth factor receptor 1 (VEGFR-1). Cell culture and gene knockout experiments indicate that each receptor contributes to different aspects of angiogenesis. KDR mediates the mitogenic function of VEGF whereas Flt-1 appears to modulate non-mitogenic functions such as those associated with cellular adhesion. Inhibiting KDR thus modulates the level of mitogenic VEGF activity. In fact, tumor growth has been shown to be susceptible to the antiangiogenic effects of VEGF receptor antagonists. (Kim et al., Nature 362, pp. 841-844, 1993).

Solid tumors can therefore be treated by tyrosine kinase inhibitors since these tumors depend on angiogenesis for the formation of the blood vessels necessary to support their growth. These solid tumors include histiocytic lymphoma, cancers of the brain, genitourinary tract, lymphatic system, stomach, larynx and lung, including lung adenocarcinoma and small cell lung cancer. Additional examples include cancers in which overexpression or activation of Raf-activating oncogenes (e.g., K-ras, erb-B) is observed. Such cancers include pancreatic and breast carcinoma. Accordingly, inhibitors of these tyrosine kinases are useful for the prevention and treatment of proliferative diseases dependent on these enzymes.

The angiogenic activity of VEGF is not limited to tumors. VEGF accounts for most of the angiogenic activity produced in or near the retina in diabetic retinopathy. This vascular growth in the retina leads to visual degeneration culminating in blindness. Ocular VEGF mRNA and protein are elevated by conditions such as retinal vein occlusion in primates and decreased $pO_2$ levels in mice that lead to neovascularization. Intraocular injections of anti-VEGF monoclonal antibodies or VEGF receptor immunofusions inhibit ocular neovascularization in both primate and rodent models. Regardless of the cause of induction of VEGF in human diabetic retinopathy, inhibition of ocular VEGF is useful in treating the disease.

Expression of VEGF is also significantly increased in hypoxic regions of animal and human tumors adjacent to areas of necrosis. VEGF is also upregulated by the expression of the oncogenes ras, raf, src and mutant p53 (all of which are relevant to targeting cancer). Monoclonal anti-VEGF antibodies inhibit the growth of human tumors in nude mice. Although these same tumor cells continue to express VEGF in culture, the antibodies do not diminish their mitotic rate. Thus tumor-derived VEGF does not function as an autocrine mitogenic factor. Therefore, VEGF contributes to tumor growth in vivo by promoting angiogenesis through its paracrine vascular endothelial cell chemotactic and mitogenic activities. These monoclonal antibodies also inhibit the growth of typically less well vascularized human colon cancers in athymic mice and decrease the number of tumors arising from inoculated cells.

Viral expression of a VEGF-binding construct of Flk-1, Flt-1, the mouse KDR receptor homologue, truncated to eliminate the cytoplasmic tyrosine kinase domains but retaining a membrane anchor, virtually abolishes the growth of a transplantable glioblastoma in mice presumably by the dominant negative mechanism of heterodimer formation with membrane spanning endothelial cell VEGF receptors. Embryonic stem cells, which normally grow as solid tumors in nude mice, do not produce detectable tumors if both VEGF alleles are knocked out. Taken together, these data indicate the role of VEGF in the growth of solid tumors. Inhibition of KDR or Flt-1 is implicated in pathological angiogenesis, and these receptors are useful in the treatment of diseases in which angiogenesis is part of the overall pathology, e.g., inflammation, diabetic retinal vascularization, as well as various forms of cancer since tumor growth is known to be dependent on angiogenesis. (Weidner et al., N. Engl. J. Med., 324, pp. 1-8, 1991).

Accordingly, the identification of small compounds which specifically inhibit, regulate and/or modulate the signal transduction of tyrosine kinases is desirable and is an object of this invention.

SUMMARY OF THE INVENTION

The present invention relates to compounds that are capable of inhibiting, modulating and/or regulating signal transduction of both receptor-type and non-receptor type tyrosine kinases. One embodiment of the present invention is illustrated by a compound of Formula I, and the pharmaceutically acceptable salts and stereoisomers thereof.

DETAILED DESCRIPTION OF THE INVENTION

The compounds of this invention are useful in the inhibition of kinases and are illustrated by a compound of Formula I:

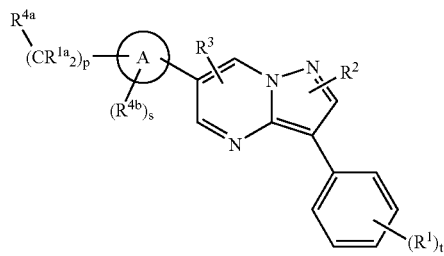

I wherein
a and b are independently 0 or 1;
m is independently 0,1 or 2;
n is 0, 1, 2, 3, 4, 5, or 6;
p is 0, 1, 2, 3, 4, 5, or 6;
s is 0, 1 or 2;
t is 0, 1, 2, or 3;

$$\text{(A)}$$

is aryl or heterocyclyl;
$R^1$ is independently selected from:
 1) $C_{1-10}$ alkyl,
 2) $C_{3-6}$ cycloalkyl,
 3) $C_{2-10}$ alkenyl,
 4) $C_{2-10}$ alkynyl,
 5) aryl,
 6) heterocyclyl,
 7) $OC_{1-6}$ alkyl-$NR^5R^6$,
 8) $NO_2$,
 9) $OR^6$, and
 10) $N(R^5)_2$,
said alkyl, cycloalkyl, alkenyl, alkynyl, aryl, and heterocyclyl is optionally substituted with one or more substituents selected from $R^7$;
$R^{1a}$ is independently selected from:
 1) H,
 2) unsubstituted or substituted $C_{1-10}$ alkyl,
 3) unsubstituted or substituted $C_{3-6}$ cycloalkyl,
 4) unsubstituted or substituted aryl, and
 5) unsubstituted or substituted heterocyclyl;
$R^2$ is:
 1) H,
 2) unsubstituted or substituted $C_{1-6}$ alkyl,
 3) $C_{1-3}$ perfluoroalkyl,
 4) $OR^6$, or
 5) halogen;
$R^3$ is:
 1) H,
 2) unsubstituted or substituted $C_{1-6}$ alkyl,
 3) $C_{1-3}$ perfluoroalkyl,
 4) $OR^6$, or
 5) halogen;
$R^{4a}$ is:
 1) $NR^5(CR^{1a}_2)_nR^8$,
 2) $NR^5(CR^{1a}_2)_nOR^5$,
 3) $R^8S(O)_mR^8$,
 4) $NR^5(CR^{1a}_2)_nC(O)NR^5R^6$,
 5) halo,
 6) $C_2$-$C_6$ alkenyl$(CR^{1a}_2)_nOR^5$,
 7) $C_2$-$C_6$ alkynyl$(CR^{1a}_2)_nOR^5$,
 8) $OR^5$,
 9) $C(O)R^5$,
 10) $R^8$,
 11) $NR^5(CR^{1a}_2)_nNR^5R^6$,
 12) $R^8C(O)NR^5(CR^{1a}_2)_nNR^5R^6$,
 13) $C(O)NR^5(CR^{1a}_2)_nR^8$,
 14) $C(O)OR^5$,
 15) $C(O)NR^5(CR^{1a}_2)_nNR^5R^6$, or
 16) $C(O)NR^5(CR^{1a}_2)_nOR^5$;
$R^{4b}$ is independently selected from:
 1) $C_{1-10}$ alkyl,
 2) $C_{3-6}$ cycloalkyl, 3) $C_{2-10}$ alkenyl,
4) $C_{2-10}$ alkynyl,
5) aryl,
6) heterocyclyl,
7) $OC_{1-6}$ alkyl-$NR^5R^6$,
8) $NO_2$,
9) $OR^6$, and
10) $NR^5R^6$, said alkyl, cycloalkyl, alkenyl, alkynyl, aryl, and heterocyclyl is optionally substituted with one or more substituents selected from $R^7$;

$R^5$ and $R^6$ are independently selected from:
1) H,
2) halo
3) aralkyl,
4) $(C=O)O_bC_1-C_{10}$ alkyl,
5) $(C=O)O_bC_3-C_8$ cycloalkyl,
6) $(C=O)O_b$aryl,
7) $(C=O)O_b$heterocyclyl,
8) $C_1-C_{10}$ alkyl,
9) aryl,
10) $C_2-C_{10}$ alkenyl,
11) $C_2-C_{10}$ alkynyl,
12) heterocyclyl,
13) $C_3-C_8$ cycloalkyl,
14) $SO_2R^a$, and
15) $(C=O)NR^b{}_2$, said alkyl, cycloalkyl, aryl, aralkyl, heterocyclyl, alkenyl, and alkynyl is optionally substituted with one or more substituents selected from $R^{7a}$, or $R^5$ and $R^6$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocylcic or bicyclic heterocycle optionally substituted with one or more substituents selected from $R^7$;

$R^7$ is independently selected from:
1) $(C=O)_aO_bC_1-C_{10}$ alkyl,
2) $(C=O)_aO_b$aryl,
3) $C_2-C_{10}$ alkenyl,
4) $C_2-C_{10}$ alkynyl,
5) $(C=O)_aO_b$ heterocyclyl,
6) $CO_2R^a$,
7) halo,
8) CN,
9) $OR^a$,
10) $O_bC_1-C_6$ perfluoroalkyl,
11) $O_a(C=O)_bNR^5R^6$,
12) oxo,
13) $C(O)R^a$,
14) $(N=O)R^5R^6$, and
15) $(C=O)_aO_bC_3-C_8$ cycloalkyl, said alkyl, aryl, alkenyl, alkynyl, heterocyclyl, and cycloalkyl optionally substituted with one or more substituents selected from $R^{7a}$;

$R^{7a}$ is independently selected from:
1) $(C=O)_aO_b(C_1-C_{10})$alkyl,
2) $O_a(C_1-C_3)$perfluoroalkyl,
3) $(C_0-C_6)$alkyl-$S(O)_mR^a$, wherein m is 0, 1, or 2,
4) oxo,
5) $OR^a$,
6) halo,
7) CN,
8) $(C_2-C_{10})$alkenyl, 9) $(C_2-C_{10})$alkynyl,
10) $(C_3-C_6)$cycloalkyl,
11) $(C_0-C_6)$alkyl-aryl,
12) $(C_0-C_6)$alkyl-heterocyclyl,
13) $(C_0-C_6)$alkyl-$N(R^b)_2$,
14) $C(O)R^a$, and
15) $(C_0-C_6)$alkyl-$CO_2H$, said alkyl, alkenyl, alkynyl, cycloalkyl, aryl, and heterocyclyl is optionally substituted with up to three substituents selected from $R^b$, OH, $(C_1-C_6)$alkoxy, halogen, $CO_2H$, CN, $O(C=O)C_1-C_6$ alkyl, oxo, $N(R^b)_2$, and —$N(R^b)$-$(C_1-C_6)$alkyl-$N(R^b)_2$;

$R^8$ is independently selected from
1) $C_1-C_{10}$ alkyl,
2) aryl,
3) heterocycle, and
4) $C_3-C_{10}$ cycloalkyl, said alkyl, aryl, heteorocyclyl, and cycloalkyl is optionally substituted with one or more substituents selected from $R^7$;

$R^a$ is independently selected from H, $(C_1-C_6)$alkyl, $(C_3-C_6)$ cycloalkyl, aryl, and heterocyclyl;

$R^b$ is independently selected from H, $(C_1-C_6)$alkyl, aryl, heterocyclyl, aralkyl, $(C_3-C_6)$cycloalkyl, $(C=O)OC_1-C_6$ alkyl, $(C=O)C_1-C_6$ alkyl and $S(O)_2R^a$ or a pharmaceutically acceptable salt or stereoisomer thereof.

A second embodiment is a compound of Formula I wherein all other substituents and variables are as defined above and, $R^1$ is independently selected from:
1) $C_{1-6}$ alkyl,
2) $C_{3-6}$ cycloalkyl,
3) $C_{1-6}$ alkoxy,
4) aryl,
5) heterocyclyl,
6) $OC_{1-6}$ alkyl-$NR^5R^6$, and
7) $OR^6$;

said alkyl, cycloalkyl, aryl, and heterocyclyl is optionally substituted with one to three substituents selected from $R^7$;

$R^2$ is:
1) H,
2) $C_{1-6}$ alkyl, or
3) $OR^6$;

$R^{4b}$ is independently selected from:
1) $C_{1-6}$ alkyl,
2) $C_{3-6}$ cycloalkyl,
3) aryl,
4) heterocyclyl,
5) $OC_{1-6}$ alkyl-$NR^5R^6$,
6) $OR^6$, and
7) $NR^5R^6$, said alkyl, cycloalkyl, aryl, and heterocyclyl is optionally substituted with one to three substituents selected from $R^7$ or a pharmaceutically acceptable salt or stereoisomer thereof.

A further embodiment of the second embodiment is a compound of Formula I, wherein all other substituents and variables are defined above and:

n is independently 0, 1, 2, 3, or 4;
s is 0 or 1;
t is 0, 1 or 2;

Ⓐ is phenyl, pyridyl, pyrimidinyl, thienyl, or pyrazinyl;

R³ is:
1) H,
2) C$_{1-6}$ alkyl, or
3) Halogen or a pharmaceutically acceptable salt or stereoisomer thereof.

A further embodiment of the above described embodiment is a compound of Formula I wherein all other substituents and variables are as defined above and, s is 0;
t is 0 or 1;
R¹ is independently selected from
1) C$_{1-6}$ allyl,
2) C$_{3-6}$ cycloalkyl,
3) OC$_{1-6}$ alkyl-NR⁵R⁶,
4) OR⁶, and
5) NR⁵R⁶, said alkyl, alkoxy and cycloalkyl is optionally substituted with one to three substituents selected from R⁷;
R² is H or C$_{1-3}$ alkyl;
R³ is H or C$_{1-3}$ alkyl;

or a pharmaceutically acceptable salt or stereoisomer thereof.

Examples of compounds of Formula I include:
1-phenyl-N-[4-(3-phenylpyrazolo[1,5-a]pyrimidin-6-yl)benzyl]methanamine;
N-[4-(3-phenylpyrazolo[1,5-a]pyrimidin-6-yl)benzyl]-N-propylamine;
N-(2-methoxyethyl)-N-[4-(3-phenylpyrazolo[1,5-a]pyrimidin-6-yl)benzyl]butan-1-amine;
N-[4-(3-phenylpyrazolo[1,5-a]pyrimidin-6-yl)benzyl]cyclopropanamine;
2-methoxy-N-[4-(3-phenylpyrazolo[1,5-a]pyrimidin-6-yl)benzyl]ethanamine;
1-[4-(3-phenylpyrazolo[1,5-a]pyrimidin-6-yl)phenyl]-N-(pyridin-3-ylmethyl)methanamine;
1-(3-{[4-(3-phenylpyrazolo[1,5-a]pyrimidin-6-yl)benzyl]amino}propyl)pyrrolidin-2-one;
1-(1-benzylpyrrolidin-3-yl)-N-[4-(3-phenylpyrazolo[1,5-a]pyrimidin-6-yl)benzyl]methanamine;
6-(4-{[4-(methylsulfonyl)piperazin-1-yl]methyl}phenyl)-3-phenylpyrazolo[1,5-a]pyrimidine;
1-[3-(3-phenylpyrazolo[1,5-a]pyrimidin-6-yl)phenyl]-N-(pyridin-3-ylmethyl)methanamine;
N-3-[3-(3-phenylpyrazolo[1,5-a]pyrimidin-6-yl)benzyl]-beta-alaninamide;
1-phenyl-N-[3-(3-phenylpyrazolo[1,5-a]pyrimidin-6-yl)benzyl]methanamine;
N-[3-(3-phenylpyrazolo[1,5-a]pyrimidin-6-yl)benzyl]-N-propylamine;
6-[4-(3-morpholin-4-ylpropyl)phenyl]-3-phenylpyrazolo[1,5-a]pyrimidine;
3-phenyl-6-[4-(3-piperidin-1-ylpropyl)phenyl]pyrazolo[1,5-a]pyrimidine;
N-1-ethyl-N-2-dimethyl-N-1-{3-[4-(3-phenylpyrazolo[1,5-a]pyrimidin-6-yl)phenyl]propyl}ethane-1,2-diamine;
N-[2-(dimethylamino)ethyl]-1-{3-[4-(3-phenylpyrazolo[1,5-a]pyrimidin-6-yl)phenyl]propyl}-D-prolinamide;
N-[2-(dimethylamino)ethyl]-1-{3-[4-(3-phenylpyrazolo[1,5-a]pyrimidin-6-yl)phenyl]propyl}-L-prolinamide;
6-{4-[(4-methylpiperazin-1-yl)carbonyl]phenyl}-3-phenylpyrazolo[1,5-a]pyrimidine;
3-phenyl-6-[4-(piperazin-1-ylcarbonyl)phenyl]pyrazolo[1,5-a]pyrimidine;
4-(3-phenylpyrazolo[1,5-a]pyrimidin-6-yl)-N-pyrrolidin-3-ylbenzamide;
6-{4-[3-(4-methylpiperazin-1-yl)-3-oxopropyl]phenyl}-3-phenylpyrazolo[1,5-a]pyrimidine;
6-[4-(3-oxo-3-piperazin-1-ylpropyl)phenyl]-3-phenylpyrazolo[1,5-a]pyrimidine;
3-[4-(3-phenylpyrazolo[1,5-a]pyrimidin-6-yl)phenyl]-N-pyrrolidin-3-ylpropanamide;
N-[2-(dimethylamino)ethyl]-4-(3-phenylpyrazolo[1,5-a]pyrimidin-6-yl)thiophene-2-carboxamide;
4-(3-phenylpyrazolo[1,5-a]pyrimidin-6-yl)-N-(pyridin-3-ylmethyl)thiophene-2-carboxamide;
N-(2-methoxyethyl)-4-(3-phenylpyrazolo[1,5-a]pyrimidin-6-yl)thiophene-2-carboxamide;
N-(3-morpholin-4-ylpropyl)-4-(3-phenylpyrazolo[1,5-a]pyrimidin-6-yl)thiophene-2-carboxamide;
N-[3-(dimethylamino)-2,2-dimethylpropyl]-4-(3-phenylpyrazolo[1,5-a]pyrimidin-6-yl)thiophene-2-carboxamide;
N-[2-(diethylamino)ethyl]-4-(3-phenylpyrazolo[1,5-a]pyrimidin-6-yl)thiophene-2-carboxamide;
N-[3-(1H-imidazol-1-yl)propyl]-4-(3-phenylpyrazolo[1,5-a]pyrimidin-6-yl)thiophene-2-carboxamide;
4-(3-phenylpyrazolo[1,5-a]pyrimidin-6-yl)-N-(2-pyridin-3-ylethyl)thiophene-2-carboxamide;
N-[2-(1-methylpyrrolidin-2-yl)ethyl]-4-(3-phenylpyrazolo[1,5-a]pyrimidin-6-yl)thiophene-2-carboxamide;
N-[(1-ethylpyrrolidin-3-yl)methyl]-4-(3-phenylpyrazolo[1,5-a]pyrimidin-6-yl)thiophene-2-carboxamide;
N-[2-(dimethylamino)ethyl]-6-(3-phenylpyrazolo[1,5-a]pyrimidin-6-yl)pyridine-2-carboxamide; or
N-(2-aminoethyl)-6-(3-phenylpyrazolo[1,5-a]pyrimidin-6-yl)pyridine-2-carboxamide;

or a pharmaceutically acceptable salt or stereoisomer thereof.

Specific compounds of the instant invention are 6-[4-(3-morpholin-4-ylpropyl)phenyl]-3-phenylpyrazolo[1,5-a]pyrimidine

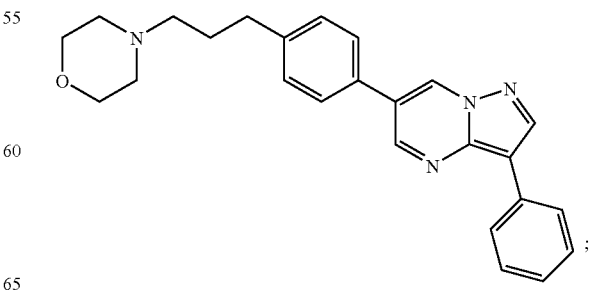
;

3-phenyl-6-[4-(3-piperidin-1-ylpropyl)phenyl]pyrazolo[1,5-a]pyrimidine

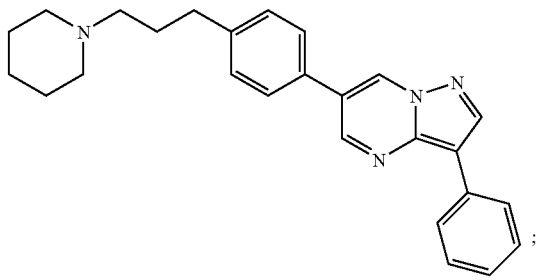

6-{4-[3-(4-methylpiperazin-1-yl)-3-oxopropyl]phenyl}-3-phenylpyrazolo[1,5-a]pyrimidine

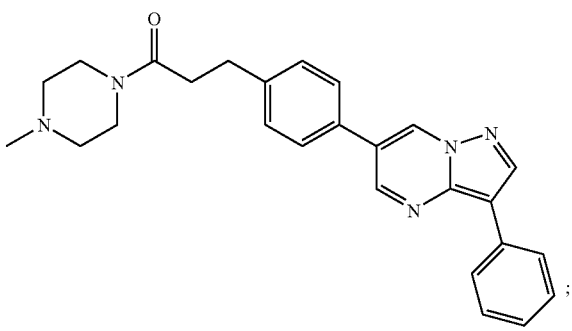

6-{4-[(4-methylpiperazin-1-yl)carbonyl]phenyl}-3-phenylpyrazolo[1,5-a]pyrimidine

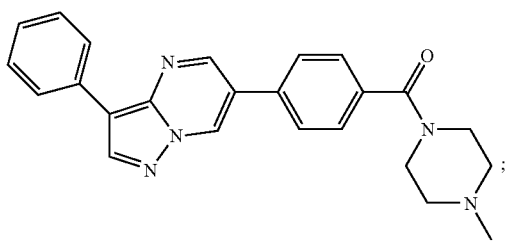

6-(4-{[4-(methylsulfonyl)piperazin-1-yl]methyl}phenyl)-3-phenylpyrazolo[1,5-a]pyrimidine

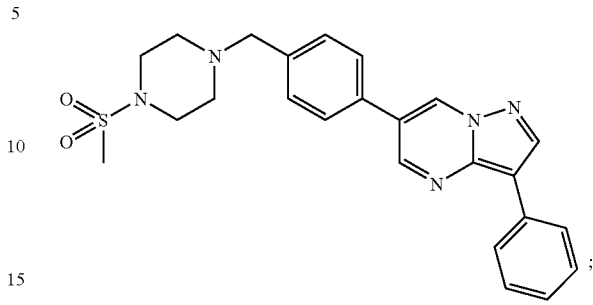

or a pharmaceutically acceptable salt or stereoisomer thereof.

Also included within the scope of the present invention is a pharmaceutical composition which is comprised of a compound of Formula I as described above and a pharmaceutically acceptable carrier. The present invention also encompasses a method of treating or preventing cancer in a mammal in need of such treatment which is comprised of administering to said mammal a therapeutically effective amount of a compound of Formula I. Preferred cancers for treatment are selected from cancers of the brain, genitourinary tract, lymphatic system, stomach, larynx and lung. Another set of preferred forms of cancer are histiocytic lymphoma, lung adenocarcinoma, small cell lung cancers, pancreatic cancer, gioblastomas and breast carcinoma.

Also included is a method of treating or preventing a disease in which angiogenesis is implicated, which is comprised of administering to a mammal in need of such treatment a therapeutically effective amount of a compound of Formula I. Such a disease in which angiogenesis is implicated is ocular diseases such as retinal vascularization, diabetic retinopathy, age-related macular degeneration, and the like.

Also included within the scope of the present invention is a method of treating or preventing inflammatory diseases which comprises administering to a mammal in need of such treatment a therapeutically effective amount of a compound of Formula 1. Examples of such inflammatory diseases are rheumatoid arthritis, psoriasis, contact dermatitis, delayed hypersensitivity reactions, and the like.

Also included is a method of treating or preventing a tyrosine kinase-dependent disease or condition in a mammal which comprises administering to a mammalian patient in need of such treatment a therapeutically effective amount of a compound of Formula I. The therapeutic amount varies according to the specific disease and is discernable to the skilled artisan without undue experimentation.

A method of treating or preventing retinal vascularization which is comprised of administering to a mammal in need of such treatment a therapeutically effective amount of compound of Formula I is also encompassed by the present invention. Methods of treating or preventing ocular diseases, such as diabetic retinopathy and age-related macular degeneration, are also part of the invention. Also included within the scope of the present invention is a method of treating or preventing inflammatory diseases, such as rheumatoid arthritis, psoriasis, contact dermatitis and delayed hypersensitivity reactions, as well as treatment or prevention of bone associated pathologies selected from osteosarcoma, osteoarthritis, and rickets.

The invention also contemplates the use of the instantly claimed compounds in combination with a second compound selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor,
10) an angiogenesis inhibitor,
11) PPAR-γ agonists,
12) PPAR-δ agonists,
13) an inhibitor of inherent multidrug resistance,
14) an anti-emetic agent,
15) an agent useful in the treatment of anemia,
16) agent useful in the treatment of neutropenia, and
17) an immunologic-enhancing drug.

Preferred angiogenesis inhibitors are selected from the group consisting of a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, and an antibody to VEGF. Preferred estrogen receptor modulators are tamoxifen and raloxifene.

Also included in the scope of the claims is a method of treating cancer which comprises administering a therapeutically effective amount of a compound of Formula 1 in combination with radiation therapy and/or in combination with a compound selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor,
10) an angiogenesis inhibitor,
11) PPAR-γ agonists,
12) PPAR-δ agonists,
13) an inhibitor of inherent multidrug resistance,
14) an anti-emetic agent,
15) an agent useful in the treatment of anemia,
16) agent useful in the treatment of neutropenia, and
17) an immunologic-enhancing drug.

And yet another embodiment of the invention is a method of treating cancer which comprises administering a therapeutically effective amount of a compound of Formula 1 in combination with paclitaxel or trastuzumab.

Also within the scope of the invention is a method of reducing or preventing tissue damage following a cerebral ischemic event which comprises administering a therapeutically effective amount of a compound of Formula I.

These and other aspects of the invention will be apparent from the teachings contained herein.

"Tyrosine kinase-dependent diseases or conditions" refers to pathologic conditions that depend on the activity of one or more tyrosine kinases. Tyrosine kinases either directly or indirectly participate in the signal transduction pathways of a variety of cellular activities including proliferation, adhesion and migration, and differentiation. Diseases associated with tyrosine kinase activities include the proliferation of tumor cells, the pathologic neovascularization that supports solid tumor growth, ocular neovascularization (diabetic retinopathy, age-related macular degeneration, and the like) and inflammation (psoriasis, rheumatoid arthritis, and the like).

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

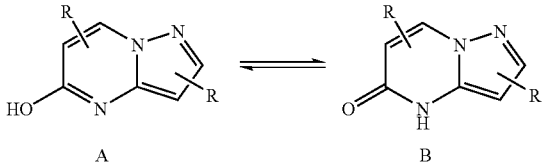

When any variable (e.g. $R^1$, $R^4$, etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is polycyclic, it is intended that the bond be attached to any of the suitable carbon atoms on the proximal ring only.

It is intended that the definition of any substituent or variable (e.g., $R^1$, $R^{1a}$, n, etc.) at a particular location in a molecule be independent of its definitions elsewhere in that molecule. Thus, $-N(R^a)_2$ represents $-NHH$, $-NHCH_3$, $-NHC_2H_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and straight-chain aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, and so on.

"Cycloalkyl" as used herein is intended to include non-aromatic cyclic hydrocarbon groups, having the specified number of carbon atoms, which may or may not be bridged or structurally constrained. Examples of such cycloalkyls include, but are not limited to, cyclopropyl, cyclobutyl, cyclopentyl, cyclohexyl, adamantyl, cyclooctyl, cycloheptyl, tetrahydro-naphthalene, methylenecylohexyl, and the like. As used herein, examples of "$C_3$-$C_{10}$ cycloalkyl" may include, but are not limited to:

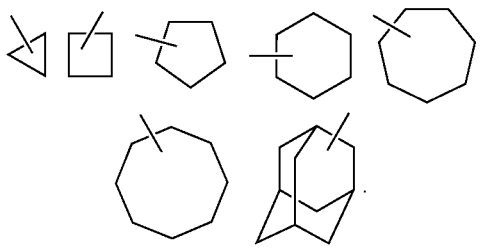

"Alkoxy" represents an alkyl group of indicated number of carbon atoms as defined above attached through an oxygen bridge.

If no number of carbon atoms is specified, the term "alkenyl" refers to a non-aromatic hydrocarbon radical, which may be branched or unbranched and cyclic or acyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl, cyclohexenyl, methylenylcyclohexenyl, and so on. As described above with respect to alkyl, the straight, branched or cyclic portion of the alkenyl group may contain double bonds and may be substituted if a substituted alkenyl group is indicated.

The term "alkynyl" refers to a hydrocarbon radical, which may be branched or unbranched and cyclic or acyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. As described above with respect to alkyl, the straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkyl-aryl. If aryl is taken to be phenyl, this definition would include phenyl itself as well as —$CH_2Ph$, —$CH_2CH_2Ph$, $CH(CH_3)CH_2CH(CH_3)Ph$, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl, indanonyl, indenyl, biphenyl, tetralinyl, tetralonyl, fluorenonyl, phenanthryl, anthryl, acenaphthyl, tetrahydronaphthyl, and the like. In cases where the aryl substituent is bicyclic, it is understood that attachment is via the phenyl ring.

As appreciated by those of skill in the art, "halo" or "halogen" as used herein is intended to include chloro, fluoro, bromo and iodo.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzodioxolyl, benzotriazolyl, benzothiofuranyl, benzothiazolyl, furanyl, thienyl, benzothienyl, benzofuranyl, benzoquinolinyl, isoquinolinyl, oxazolyl, isoxazolyl, indolyl, pyrazinyl, pyridazinyl, pyridinyl, pyrimidinyl, pyrrolyl, quinolinyl, tetrahydronaphthyl, tetrahydroquinoline, and the like.

The term heterocycle or heterocyclic or heterocyclyl, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. "Heterocycle" or "heterocyclyl" therefore includes the above mentioned heteroaryls, as well as dihydro and tetrathydro analogs thereof. Further examples of "heterocyclyl" include, but are not limited to the following: benzodioxolyl, benzofuranyl, benzofurazanyl, benzimidazolyl, benzopyranyl, benzopyrazolyl, benzotriazolyl, benzothiazolyl, benzothienyl, benzothiofuranyl, benzothiophenyl, benzothiopyranyl, benzoxazolyl, carbazolyl, carbolinyl, chromanyl, cinnolinyl, diazapinonyl, dihydrobenzodioxinyl, dihydrobenzofuranyl, dihydrobenzofuryl, dihydrobenzoimidazolyl, dihydrobenzothienyl, dihydrobenzothiopyranyl, dihydrobenzothiopyranyl sulfone, dihydrobenzothiophenyl, dihydrobenzoxazolyl, dihydrocyclopentapyridinyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dioxanyl, dioxidotetrahydrothienyl, furyl, furanyl, imidazolyl, imidazolinyl, imidazolidinyl, imidazothiazolyl, imidazopyridinyl, indazolyl, indolazinyl, indolinyl, indolyl, isobenzofuranyl, isochromanyl, isoindolyl, isoindolinyl, isoquinolinone, isoquinolyl, isothiazolyl, isothiazolidinyl, isoxazolinyl, isoxazolyl, methylenedioxybenzoyl, morpholinyl, naphthpyridinyl, oxadiazolyl, oxazolyl, oxazolinyl, oxetanyl, oxoazepinyl, oxadiazolyl, oxodihydrophthalazinyl, oxodihydroindolyl, oxodihydrotriazolyl, oxoimidazolidinyl, oxopiperazinyl, oxopiperdinyl, oxopyrrolidinyl, oxopyrimidinyl, oxopyrrolyl, oxotriazolyl, piperidyl, piperidinyl, piperazinyl, pyranyl, pyrazinyl, pyrazolyl, pyridazinyl, pyridinonyl, pyridopyridinyl, pyridazinyl, pyridyl, pyridinyl, pyrimidinyl, pyrrolyl, pyrrolidinyl, quinazolinyl, quinolinyl, quinolyl, quinolinonyl, quinoxalinyl, tetrahydrobenzoannulenyl, tetrahydrocycloheptapyridinyl, tetrahydrofuranyl, tetrahydrofuryl, tetrahydroisoquinolinyl, tetrahydropyranyl, tetrahydroquinolinyl, tetrazolyl, tetrazolopyridyl, thiadiazolyl, thiazolyl, thiazolinyl, thienofuryl, thienyl, triazolyl, azetidinyl, 1,4-dioxanyl, hexahydroazepinyl, and the like. Preferably, heterocycle is selected from oxoazepinyl, benzimidazolyl, dioxanyl, dihydrobenzodioxinyl, dihydroindolyl, Dihydrotriazolyl, dioxanyl, dioxidotetrahydrothienyl, oxetanyl, piperidinyl, pyrazolyl, pyridinyl, tetrahydrobenzoannulenyl, tetrahydrofuranyl, tetrahydropyranyl, tetrazolyl, imidazolyl, indolyl, isoquinolinyl, morpholinyl, piperidyl, piperazinyl, pyridyl, pyrrolidinyl, oxopiperidinyl, oxopyrrolidinyl, quinolinyl, tetrahydrofuryl, tetrahydroisoquinolinyl, thienyl, and triazolyl.

As used herein, "aralkyl" is intended to mean an aryl moiety, as defined above, attached through a $C_1$-$C_{10}$ alkyl linker, where alkyl is defined above. Examples of aralkyls include, but are not limited to, benzyl, naphthylmethyl and phenylpropyl.

As used herein, "heterocyclylalkyl" is intended to mean a heterocyclic moiety, as defined below, attached through a $C_1$-$C_{10}$ alkyl linker, where alkyl is defined above. Examples of heterocyclylalkyls include, but are not limited to, pyridylmethyl, imidazolylethyl, pyrrolidinylmethyl, morpholinylethyl, quinolinylmethyl, imidazolylpropyl and the like.

As used herein, the terms "substituted $C_1$-$C_{10}$ alkyl" and "substituted $C_1$-$C_6$ alkoxy" are intended to include the branch or straight-chain alkyl group of the specified number of carbon atoms, wherein the carbon atoms may be substituted with 1 to 3 substituents selected from the group which includes, but is not limited to, halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

As used herein, the terms "substituted $C_3$-$C_{10}$ cycloalkyl", "substituted aryl", "substituted heterocycle", "substituted aralkyl" and "substituted heterocyclylalkyl" are intended to include the cyclic group containing from 1 to 3 substituents in addition to the point of attachment to the rest of the compound. Preferably, the substituents are selected from the group which includes, but is not limited to, halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

As used herein, the phrase "substituted with at least one substituent" is intended to mean that the substituted group being referenced has from 1 to 6 substituents. Preferably, the substituted group being referenced contains from 1 to 3 substituents, in addition to the point of attachment to the rest of the compound.

In an aspect of the invention, $R^2$ and $R^3$ are H.

In an aspect of the invention,

is phenyl, thienyl or pyridyl.

In an aspect of the invention, s and t are 0.

In certain instances, $R^5$ and $R^6$ are defined such that they can be taken together with the nitrogen to which they are attached to form a monocyclic or bicyclic heterocycle with 5-7 members in each ring and optionally containing, in addition to the nitrogen, one or two additional heteroatoms selected from N, O and S, said heterocycle optionally substituted with one or more substituents selected from $R^{7a}$. Examples of the heterocycles that can thus be formed include, but are not limited to the following, keeping in mind that the heterocycle is optionally substituted with one or more substituents chosen from $R^{7a}$:

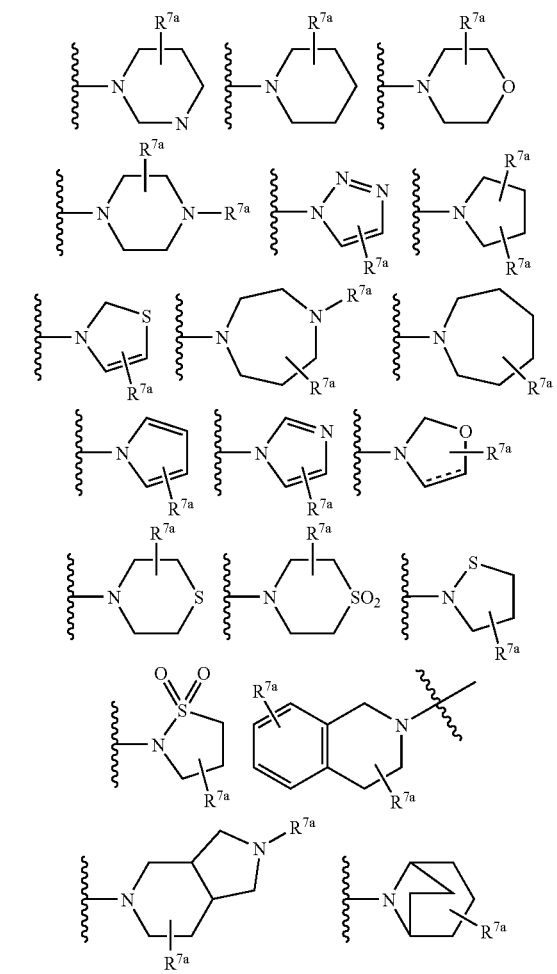

It is intended that the definition of any substituent or variable (e.g., $R^1$, $R^{1a}$, n, etc.) at a particular location in a molecule be independent of its definitions elsewhere in that molecule. Thus, —N($^4$)$_2$ represents —NHH, —NHCH$_3$, —NHC$_2$H$_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

For use in medicine, the salts of the compounds of Formula I will be pharmaceutically acceptable salts. Other salts may, however, be useful in the preparation of the compounds according to the invention or of the their pharmaceutically acceptable salts. When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The preparation of the pharmaceutically acceptable salts described above and other typical pharmaceutically acceptable salts is more fully described by Berg et al., "Pharmaceutical Salts," J. Pharm. Sci., 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

Abbreviations, which may be used in the description of the chemistry and in the Examples that follow, include:
Ac$_2$O Acetic anhydride;
AcOH Acetic acid;
AIBN 2,2'-Azobisisobutyronitrile;
Ar Aryl;
BINAP 2,2'-Bis(diphenylphosphino)-1,1' binaphthyl;
Bn Benzyl;
BOC/Boc tert-Butoxycarbonyl;
BSA Bovine Serum Albumin;
CAN Ceric Ammonia Nitrate;
CBz Carbobenzyloxy;
CI Chemical Ionization;
DBAD Di-tert-butyl azodicarboxylate;
DBU 1,8-Diazabicyclo[5.4.0]undec-7-ene;
DCC 1,3 Dichlorohexylcarbodiimide;
DCE 1,2-Dichloroethane;
DCM Dichloromethane;
DIEA N,N-Diisopropylethylamine;
DMAP 4-Dimethylaminopyridine;
DME 1,2-Dimethoxyethane;
DMF N,N-Dimethylformamide;
DMSO Methyl sulfoxide;
DPPA Diphenylphosphoryl azide;
DTT Dithiothreitol;
EDC 1-(3-Dimethylaminopropyl)-3-ethyl-carbodiimide-hydrochloride;
EDTA Ethylenediaminetetraacetic acid;
ELSD Evaporative Light Scattering Detector;
ES Electrospray;
ESI Electrospray ionization;
Et$_2$O Diethyl ether;
Et$_3$N Triethylamine;
EtOAc Ethyl acetate;
EtOH Ethanol;
FAB Fast atom bombardment;
HEPES 4-(2-Hydroxyethyl)-1-piperazineethanesulfonic acid;
HMPA Hexamethylphosphoramide;
HOAc Acetic acid;
HOBT 1-Hydroxybenzotriazole hydrate;
HOOBT 3-Hydroxy-1,2,2-benzotriazin-4(3H)-one;
HPLC High-performance liquid chromatography;
HRMS High Resolution Mass Spectroscopy;
KOtBu Potassium tert-butoxide;
LAH Lithium aluminum hydride;
LCMS Liquid Chromatography Mass Spectroscopy;
MCPBA m-Chloroperoxybenzoic acid;
Me Methyl;
MeOH Methanol;
Ms Methanesulfonyl;
MS Mass Spectroscopy;
MsCl Methanesulfonyl chloride;
n-Bu n-butyl;
n-Bu$_3$P Tri-n-butylphosphine;
NaHMDS Sodium bis(trimethylsilyl)amide;
NBS N-Bromosuccinimide;
NMM N-methylmorpholine;
NMR Nuclear Magnetic Resonance;
Pd(PPh$_3$)$_4$ Palladium tetrakis(triphenylphosphine);
Pd$_2$(dba)$_3$ Tris(dibenzylideneacetone)dipalladium (0)
Ph Phenyl;
PMSF α-Toluenesulfonyl fluoride;
PS-DCC Polystyrene dicyclohexylcarbodiimide;
PS-DMAP Polystyrene dimethylaminopyridine;
PS-NMM Polystyrene N-methylmorpholine;
Py or pyr Pyridine;
PYBOP Benzotriazol-1-yloxytripyrrolidinophosphonium (or PyBOP)hexafluorophosphate;
RPLC Reverse Phase Liquid Chromatography;
RT Room Temperature;
SCX SPE Strong Cation Exchange Solid Phase Extraction;
t-Bu tert-Butyl;
TBAF Tetrabutylammonium fluoride;
TBSCl tert-Butyldimethylsilyl chloride;
TFA Trifluoroacetic acid;
THF Tetrahydrofuran;

TIPS Triisopropylsilyl;
TMS Tetramethylsilane; and
Tr Trityl.

The compounds of this invention may be prepared by employing reactions as shown in the following schemes, in addition to other standard manipulations that are known in the literature or exemplified in the experimental procedures. These schemes, therefore, are not limited by the compounds listed nor by any particular substituents employed for illustrative purposes. Substituent numbering as shown in the schemes do not necessarily correlate to that used in the claims.

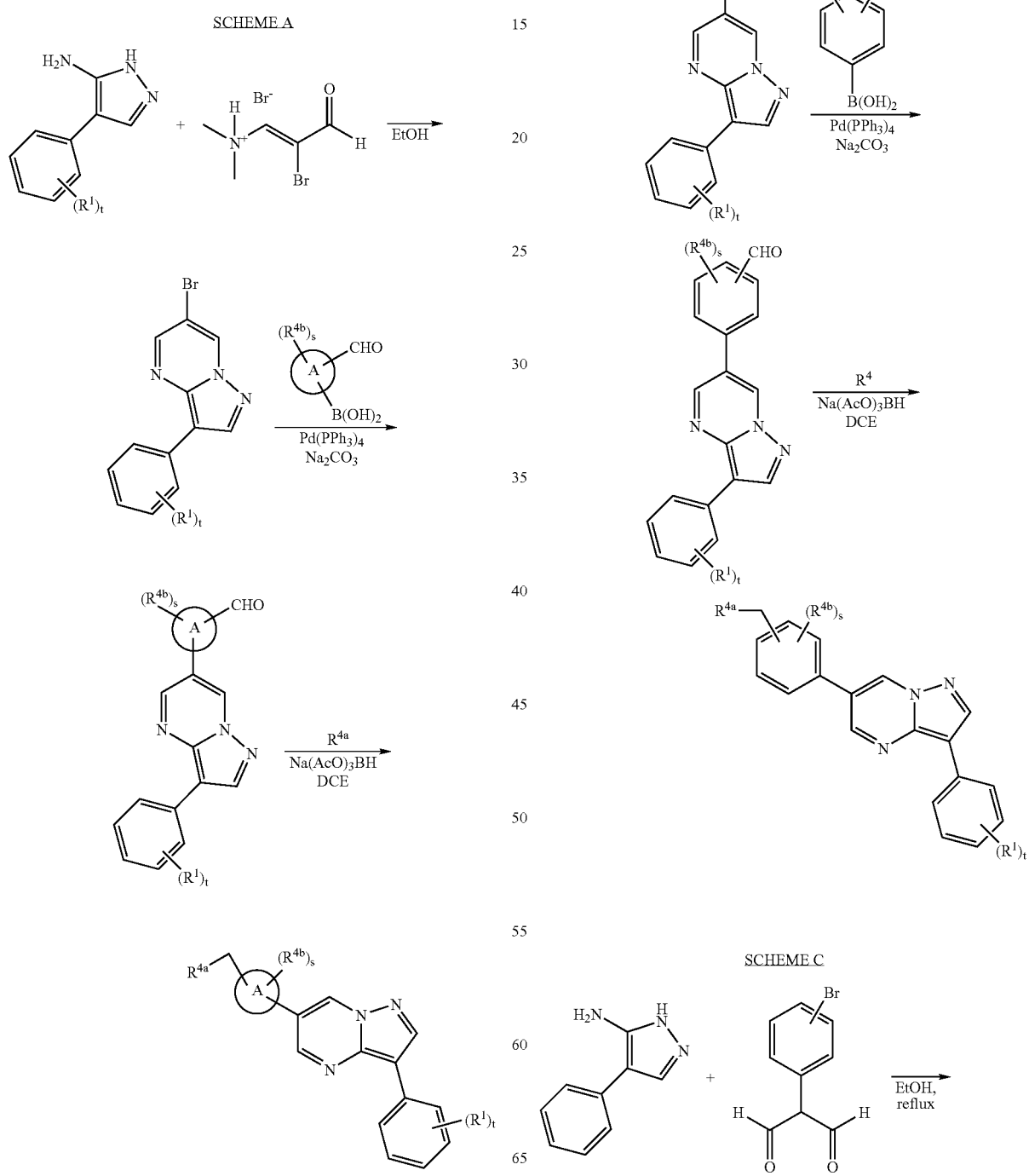

-continued

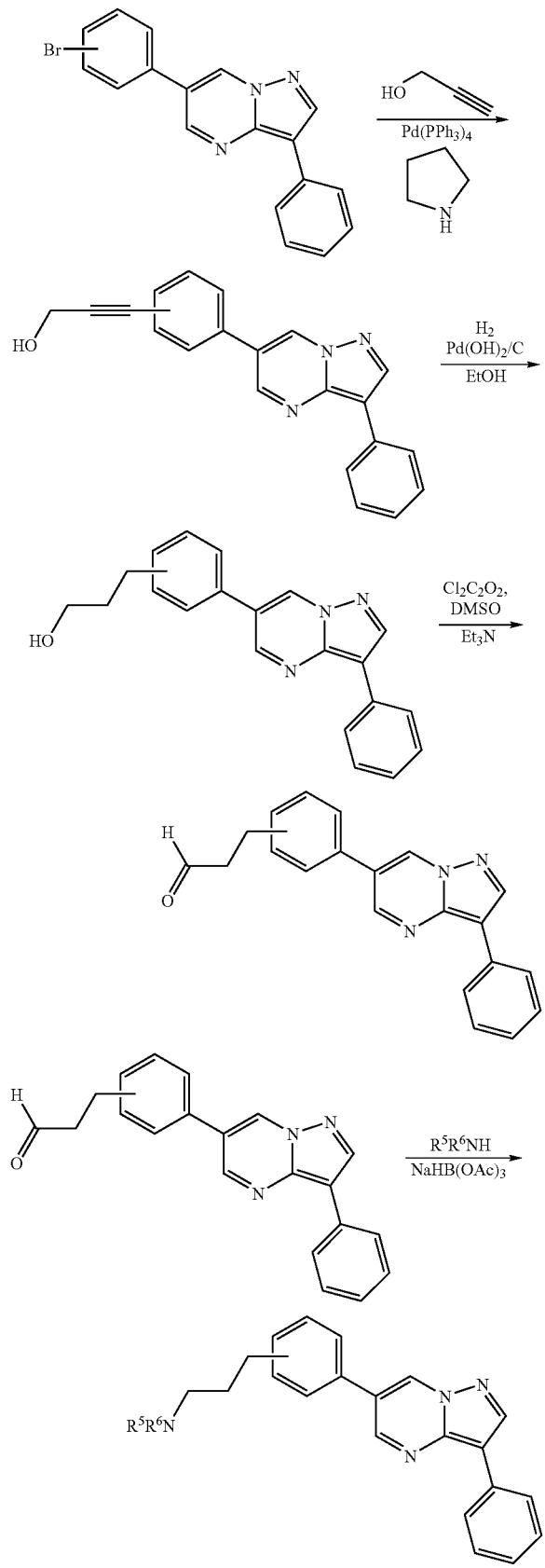

SCHEME D

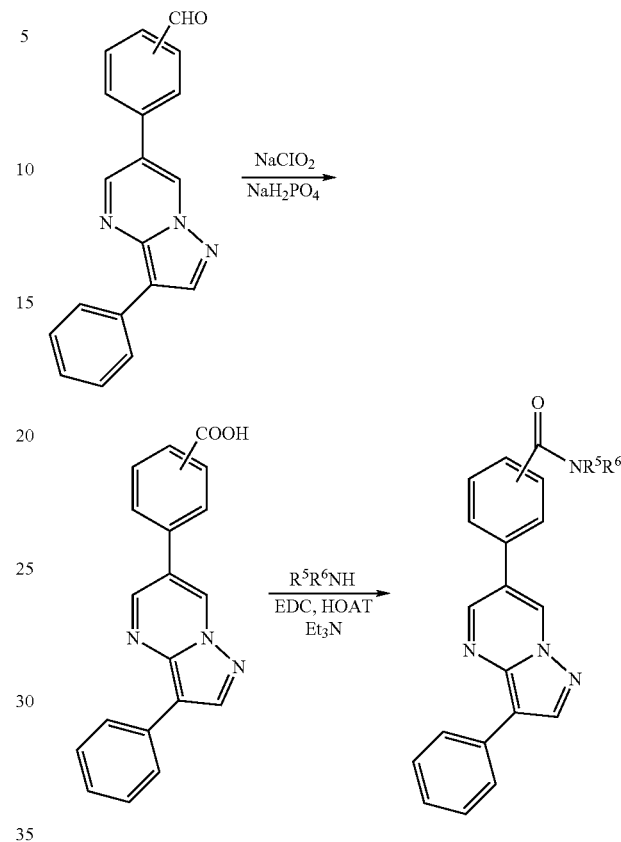

Utility

The instant compounds are useful as pharmaceutical agents for mammals, especially for humans, in the treatment of tyrosine kinase dependent diseases. Such diseases include the proliferation of tumor cells, the pathologic neovascularization (or angiogenesis) that supports solid tumor growth, ocular neovascularization (diabetic retinopathy, age-related macular degeneration, and the like) and inflammation (psoriasis, rheumatoid arthritis, and the like).

The compounds of the instant invention may be administered to patients for use in the treatment of cancer. The instant compounds inhibit tumor angiogenesis, thereby affecting the growth of tumors (J. Rak et al. *Cancer Research*, 55:4575-4580, 1995). The anti-angiogenesis properties of the instant compounds are also useful in the treatment of certain forms of blindness related to retinal vascularization.

The disclosed compounds are also useful in the treatment of certain bone-related pathologies, such as osteosarcoma, osteoarthritis, and rickets, also known as oncogenic osteomalacia. (Hasegawa et al., Skeletal Radiol., 28, pp. 41-45, 1999; Gerber et al., Nature Medicine, Vol. 5, No. 6, pp. 623-628, June 1999). And since VEGF directly promotes osteoclastic bone resorption through KDR/Flk-1 expressed in mature osteoclasts (FEBS Let. 473:161-164 (2000); Endocrinology, 141:1667 (2000)), the instant compounds are also useful to treat and prevent conditions related to bone resorption, such as osteoporosis and Paget's disease.

The claimed compounds can also be used to reduce or prevent tissue damage which occurs after cerebral ischemic events, such as stroke, by reducing cerebral edema, tissue damage, and reperfusion injury following ischemia. (*Drug News Perspect* 11:265-270 (1998); *J. Clin. Invest.* 104:1613-1620 (1999); *Nature Med* 7:222-227 (2001)).

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and cornstarch, and lubricating agents, such as magnesium stearate, are commonly added. For oral administration in capsule form, useful diluents include lactose and dried cornstarch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The instant compounds may also be co-administered with other well known therapeutic agents that are selected for their particular usefulness against the condition that is being treated.

For example, the instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors and agents that interfere with cell cycle checkpoints. The instant compounds are particularly useful when co-administered with radiation therapy. The synergistic effects of inhibiting VEGF in combination with radiation therapy have been described in the art. (See WO 00/61186).

"Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, anti-metabolites; biological response modifiers; hormonal/anti-hormonal therapeutic agents, haematopoietic growth factors, monoclonal antibody targeted therapeutic agents and topoisomerase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston-3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, G1331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydro0xy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino] benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768 and WO 01/98278, and pending U.S. Ser. Nos. 60/338,779 (filed Dec. 6, 2001), 60/338,344 (filed Dec. 6, 2001), 60/338,383 (filed Dec. 6, 2001), 60/338,380 (filed Dec. 6, 2001), 60/338,379 (filed Dec. 6, 2001) and 60/344,453 (filed Nov. 7, 2001).

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl CoA reductase. Compounds which have inhibitory activity for HMG CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAY-CHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

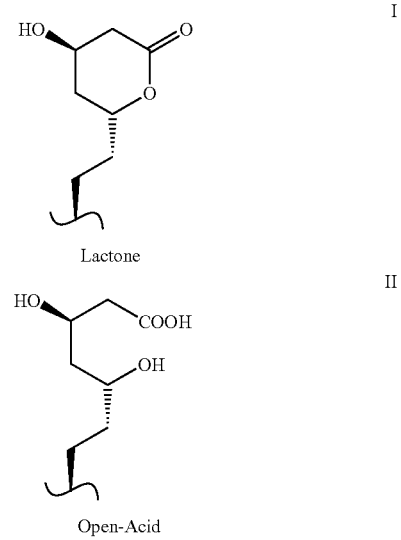

Lactone

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenz-imidazole, diethylamine, piperazine, and tris(hydroxymethyl)aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]-4-(3-chlorophenyl)-1-methyl-2(1H)-quinolinone, (−)-6-[amino(4-chlorophenyl)(1-methyl-1H-imidazol-5-yl)methyl]-4-(3-chlorophenyl)-1-methyl-2(1H)-quinolinone, (+)-6-[amino(4-chlorophenyl)(1-methyl-1H-imidazol-5-yl)methyl]-4-(3-chlorophenyl)-1-methyl-2(1H)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)methyl]-2-piperazinone, 5(S)-n-Butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{5-[4-hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2']bipyridin-5'-ylmethyl]-3H-imidazol-4-ylmethyl}benzonitrile, 4-{3-[4-(2-oxo-2H-[1,2']bipyridin-5'-ylmethyl]-3H-imidazol-4-ylmethyl}benzonitrile, 4-[3-(2-oxo-1-phenyl-1,2-dihydropyridin-4-ylmethyl)-3H-imidazol-4-ylmethyl}benzonitrile, 18,19-dihydro-19-oxo-5H,17H-6,10:12,16-dimetheno-1H-imidazo[4,3-c][1,11,4]dioxaazacyclo-nonadecine-9-carbonitrile, (±)-19,20-dihydro-19-oxo-5H-18,21-ethano-12,14-etheno-6,10-metheno-22H-benzo[d]imidazo[4,3-k][1,6,9,12]oxatriazacyclooctadecine-9-carbonitrile, 19,20-dihydro-19-oxo-5H, 17H-18,21-ethano-6,10:12,16-dimetheno-22H-imidazo[3,4-h][1,8,11,14]oxatriazacycloeicosine-9-carbonitrile, and (±)-19,20dihydro-3-methyl-19-oxo-5H-18,21-ethano-12,14-etheno-6,10-metheno-22H-benzo[d]imidazo[4,3-k][1,6,9,12]oxa-triazacyclooctadecine-9-carbonitrile.

Other examples of prenyl-protein transferase inhibitors can be found in the following publications and patents: WO 96/30343, WO 97/18813,.WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-$\alpha$, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101: 329-354 (2001)). TAFIa inhibitors have been described in U.S. Ser. Nos. 60/310,927 (filed Aug. 8, 2001) and 60/349, 925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC$_{202}$ (Cyclacel) and BMS-387032.

As described above, the combinations with NSAID's are directed to the use of NSAID's which are potent COX-2 inhibiting agents. For purposes of this specification an NSAID is potent if it possess an IC$_{50}$ for the inhibition of COX-2 of 1 μM or less as measured by cell or microsomal assays.

Additionally, in the case of bone-related disorders, combinations that would be useful include those with antiresorptive bisphosphonates, such as alendronate and risedronate; integrin blockers (defined further below), such as $\alpha_v\beta_3$ antagonists; conjugated estrogens used in hormone replacement therapy, such as PREMPRO®, PREMARIN® and ENDOMETRION®; selective estrogen receptor modulators (SERMs), such as raloxifene, droloxifene, CP-336, 156 (Pfizer) and lasofoxifene; cathespin K inhibitors; and ATP proton pump inhibitors.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of IC$_{50}$ for COX-2 over IC$_{50}$ for COX-1 evaluated by cell or microsomal assays. Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference.

Inhibitors of COX-2 that are particularly useful in the instant method of treatment are:

3-phenyl-4-(4-(methylsulfonyl)phenyl)-2-(5H)-furanone; and

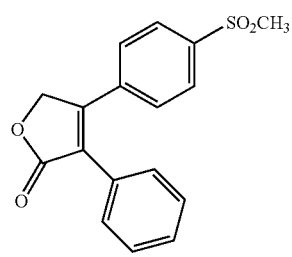

5-chloro-3-(4-methylsulfonyl)phenyl-2-(2-methyl-5-pyridinyl)pyridine;

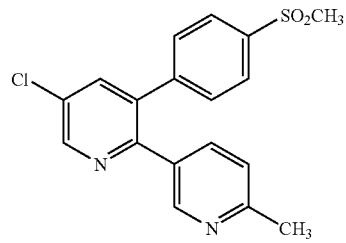

or a pharmaceutically acceptable salt thereof.

General and specific synthetic procedures for the preparation of the COX-2 inhibitor compounds described above are found in U.S. Pat. No. 5,474,995, issued Dec. 12, 1995, U.S. Pat. No. 5,861,419, issued Jan. 19, 1999, and U.S. Pat. No. 6,001,843, issued Dec. 14, 1999, all of which are herein incorporated by reference.

Compounds that have been described as specific inhibitors of COX-2 and are therefore useful in the present invention include, but are not limited to, the following:

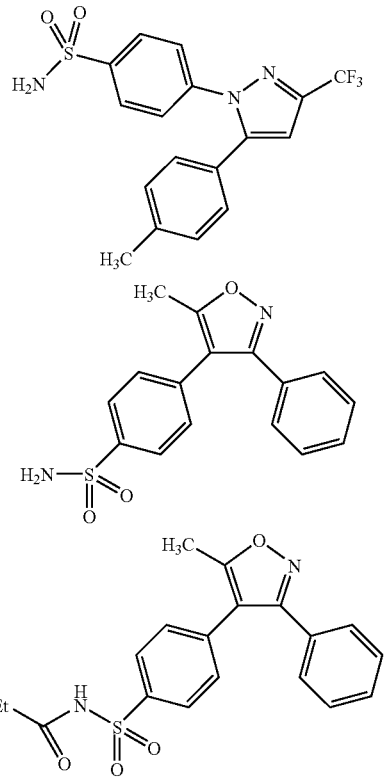

or a pharmaceutically acceptable salt thereof.

Compounds which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999.

Compounds which are specific inhibitors of COX-2 and are therefore useful in the present invention, and methods of synthesis thereof, can be found in the following patents, pending applications and publications, which are herein incorporated by reference: U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20, 1998.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide,CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-$\gamma$ (i.e., PPAR-gamma) agonists and PPAR-$\delta$ (i.e., PPAR-delta) agonists are useful in the treatment of certain malingnancies. PPAR-$\gamma$ and PPAR-$\delta$ are the nuclear peroxisome proliferator-activated receptors $\gamma$ and $\delta$. The expression of PPAR-$\gamma$ on endothelial cells and its involvement in angiogenesis has been reported in the literature (see *J. Cardiovasc. Pharmacol.* 1998; 31:909-913; *J. Biol. Chem.* 1999;274:9116-9121; *Invest. Ophthalmol Vis. Sci.* 2000; 41:2309-2317). More recently, PPAR-$\gamma$ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-$\gamma$ agonists and PPAR-$\gamma/\alpha$ agonists include, but are not limited to, thiazolidinediones (such as DRF2725, CS-011, troglitazone, rosiglitazone, and pioglitazone), fenofibrate, gemfibrozil, clofibrate, GW2570, SB219994; AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (Am J Hum Genet 61:785-789, 1997) and Kufe et al (Cancer Medicine, 5th Ed, pp 876-889, B C Decker, Hamilton 2000). Gene therapy can be used to deliver any tumor suppressing gene. Examples of such genes include, but are not limited to, p 53, which can be delivered via recombinant virus-mediated gene transfer (see U.S. Pat. No. 6,069,134, for example) a uPA/uPAR antagonist ("Adenovirus Mediated Delivery of a uPA/uPAR Antagonist Suppresses Angiogenesis-Dependent Tumor Growth and Dissemination in Mice," Gene Therapy, August 1998;5(8):1105-13), and interferon gamma (J Immunol 2000;164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. For the treatment or prevention of emesis that may result upon administration of the instant compounds, conjunctive therapy with an anti-emesis agent selected from a neurokinin-1 receptor antagonist, a 5HT3 receptor antagonist and a corticosteroid is preferred.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96137489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

A particularly preferred neurokinin-1 receptor antagonist for use in conjunction with the compounds of the present invention is 2-(R)-(1-(R)-(3,5-bis(trifluoromethyl)phenyl) ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

Thus, the scope of the instant invention encompasses the use of the instantly claimed compounds in combination with a second compound selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor,
10) an angiogenesis inhibitor,
11) PPAR-γ agonists,
12) PPAR-δ agonists,
13) an inhibitor of inherent multidrug resistance,
14) an anti-emetic agent,
15) an agent useful in the treatment of anemia,
16) agent useful in the treatment of neutropenia, and
17) an immunologic-enhancing drug.

Preferred angiogenesis inhibitors to be used as the second compound are a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. Preferred estrogen receptor modulators are tamoxifen and raloxifene.

Also included in the scope of the claims is a method of treating cancer that comprises administering a therapeutically effective amount of a compound of Formula I in combination with radiation therapy and/or in combination with a compound selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor,
10) an angiogenesis inhibitor,
11) PPAR-γ agonists,
12) PPAR-δ agonists,
13) an inhibitor of inherent multidrug resistance,
14) an anti-emetic agent,
15) an agent useful in the treatment of anemia,
16) agent useful in the treatment of neutropenia, and
17) an immunologic-enhancing drug.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a compound selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor, 9) a reverse transcriptase inhibitor,
10) an angiogenesis inhibitor, and
11) a PPAR-γ agonist, and
12) PPAR-δ agonists.

Examples of HIV protease inhibitors include amprenavir, abacavir, CGP-73547, CGP-61755, DMP450, indinavir, nelfinavir, tipranavir, ritonavir, saquinavir, ABT-378, AG 1776, and BMS-232,632. Examples of reverse transcriptase inhibitors include delaviridine, efavirenz, GS-840, HB Y097, lamivudine, nevirapine, AZT, 3TC, ddC, and ddI.

The instant compounds are also useful, alone or in combination with platelet fibrinogen receptor (GP IIb/IIIa) antagonists, such as tirofiban, to inhibit metastasis of cancerous cells. Tumor cells can activate platelets largely via thrombin generation. This activation is associated with the release of VEGF. The release of VEGF enhances metastasis by increasing extravasation at points of adhesion to vascular endothelium (Amirkhosravi, *Platelets* 10, 285-292, 1999). Therefore, the present compounds can serve to inhibit metastasis, alone or in combination with GP IIb/IIIa) antagonists. Examples of other fibrinogen receptor antagonists include abciximab, eptifibatide, sibrafiban, lamifiban, lotrafiban, cromofiban, and CT50352.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

Assays

The compounds of the instant invention described in the Examples were tested by the assays described below and were found to have kinase inhibitory activity. Other assays are known in the literature and could be readily performed by those of skill in the art. (see, for example, Dhanabal et al., *Cancer Res.* 59:189-197; Xin et al., *J. Biol. Chem.* 274: 9116-9121; Sheu et al., *Anticancer Res.* 18:4435-4411; Ausprunk et al., *Dev. Biol.* 38:237-248; Gimbrone et al., *J. Natl. Cancer Inst.* 52:413-427; Nicosia et al., In *Vitro* 18:538-549.)

I. VEGF Receptor Kinase Assay

VEGF receptor kinase activity is measured by incorporation of radio-labeled phosphate into polyglutamic acid, tyrosine, 4:1 (pEY) substrate. The phosphorylated pEY product is trapped onto a filter membrane and the incorporation of radio-labeled phosphate quantified by scintillation counting.

Materials

VEGF Receptor Kinase

The intracellular tyrosine kinase domains of human KDR (Terman, B. I. et al. Oncogene (1991) vol. 6, pp. 1677-1683.) and Flt-1 (Shibuya, M. et al. Oncogene (1990) vol. 5, pp. 519-524) were cloned as glutathione S-transferase (GST) gene fusion proteins. This was accomplished by cloning the cytoplasmic domain of the KDR kinase as an in frame fusion at the carboxy terminus of the GST gene. Soluble recombinant GST-kinase domain fusion proteins were expressed in Spodoptera frugiperda (Sf21) insect cells (Invitrogen) using a baculovirus expression vector (pAcG2T, Pharmingen).

The other materials used and their compositions were as follows:

Lysis buffer: 50 mM Tris pH 7.4, 0.5 M NaCl, 5 mM DTT, 1 mM EDTA, 0.5% triton X-100, 10% glycerol, 10 mg/mL of each leupeptin, pepstatin and aprotinin and 1 mM phenylmethylsulfonyl fluoride (all Sigma).

Wash buffer: 50 mM Tris pH 7.4, 0.5 M NaCl, 5 mM DTT, 1 mM EDTA, 0.05% triton X-100, 10% glycerol, 10 mg/mL of each leupeptin, pepstatin and aprotinin and 1 mM phenylmethylsulfonyl fluoride.

Dialysis buffer: 50 mM Tris pH 7.4, 0.5 M NaCl, 5 mM DTT, 1 mM EDTA, 0.05% triton X-100, 50% glycerol, 10 mg/mL of each leupeptin, pepstatin and aprotinin and 1 mM phenylmethylsuflonyl fluoride.

10× reaction buffer: 200 mM Tris, pH 7.4, 1.0 M NaCl, 50 mM $MnCl_2$, 10 mM DTT and 5 mg/mL bovine serum albumin (Sigma).

Enzyme dilution buffer: 50 mM Tris, pH 7.4, 0.1 M NaCl, 1 mM DTT, 10% glycerol, 100 mg/mL BSA.

10× Substrate: 750 μg/mL poly (glutamic acid, tyrosine; 4:1) (Sigma).
Stop solution: 30% trichloroacetic acid, 0.2 M sodium pyrophosphate (both Fisher).
Wash solution: 15% trichloroacetic acid, 0.2 M sodium pyrophosphate.
Filter plates: Millipore #MAFC NOB, GF/C glass fiber 96 well plate.

Method

A. Protein Purification

1. Sf21 cells were infected with recombinant virus at a multiplicity of infection of 5 virus particles/cell and grown at 27° C. for 48 hours.

2. All steps were performed at 4° C. Infected cells were harvested by centrifugation at 1000×g and lysed at 4° C. for 30 minutes with 1/10 volume of lysis buffer followed by centrifugation at 100,000×g for 1 hour. The supernatant was then passed over a glutathione Sepharose column (Pharmacia) equilibrated in lysis buffer and washed with 5 volumes of the same buffer followed by 5 volumes of wash buffer. Recombinant GST-KDR protein was eluted with wash buffer/10 mM reduced glutathione (Sigma) and dialyzed against dialysis buffer.

B. VEGF Receptor Kinase Assay

1. Add 5 μl of inhibitor or control to the assay in 50% DMSO.
2. Add 35 μl of reaction mix containing 5 μl of 10× reaction buffer, 5 μl 25 mM ATP/10 μCi [$^{33}$P]ATP (Amersham), and 5 μl 10× substrate.
3. Start the reaction by the addition of 10 μl of KDR (25 nM) in enzyme dilution buffer.
4. Mix and incubate at room temperature for 15 minutes.
5. Stop by the addition of 50 μl stop solution.
6. Incubate for 15 minutes at 4° C.
7. Transfer a 90 μl aliquot to filter plate.
8. Aspirate and wash 3 times with wash solution.
9. Add 30 μl of scintillation cocktail, seal plate and count in a Wallac Microbeta scintillation counter.

II. Human Umbilical Vein Endothelial Cell Mitogenesis Assay

Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H]thymidine into cellular DNA.

Materials

HUVECs: HUVECs frozen as primary culture isolates are obtained from Clonetics Corp. Cells are maintained in Endothelial Growth Medium (EGM; Clonetics) and are used for mitogenic assays described in passages 3-7 below.
Culture Plates: NUNCLON 96-well polystyrene tissue culture plates (NUNC #167008).
Assay Medium: Dulbecco's modification of Eagle's medium containing 1 g/mL glucose (low-glucose DMEM; Mediatech) plus 10% (v/v) fetal bovine serum (Clonetics).
Test Compounds: Working stocks of test compounds are diluted serially in 100% dimethylsulfoxide (DMSO) to 400-fold greater than their desired final concentrations. Final dilutions to 1× concentration are made directly into Assay Medium immediately prior to addition to cells.
10× Growth Factors: Solutions of human VEGF$_{165}$ (500 ng/mL; R&D Systems) and bFGF (10 ng/mL; R&D Systems) are prepared in Assay Medium.
10× [$^3$H]Thymidine: [Methyl-$^3$H]thymidine (20 Ci/mmol; Dupont-NEN) is diluted to 80 μCi/mL in low-glucose DMEM.
Cell Wash Medium: Hank's balanced salt solution (Mediatech) containing 1 mg/mL bovine serum albumin (Boehringer-Mannheim).
Cell Lysis Solution: 1 N NaOH, 2% (w/v) Na$_2$CO$_3$.

Method

1. HUVEC monolayers maintained in EGM are harvested by trypsinization and plated at a density of 4000 cells per 100 μL Assay Medium per well in 96-well plates. Cells are growth-arrested for 24 hours at 37° C. in a humidified atmosphere containing 5% CO$_2$.

2. Growth-arrest medium is replaced by 100 μL Assay Medium containing either vehicle (0.25% [v/v] DMSO) or the desired final concentration of test compound. All determinations are performed in triplicate. Cells are then incubated at 37° C. with 5% CO$_2$ for 2 hours to allow test compounds to enter cells.

3. After the 2-hour pretreatment period, cells are stimulated by addition of 10 μl/well of either Assay Medium, 10× VEGF solution or 10× bFGF solution. Cells are then incubated at 37° C. and 5% CO$_2$.

4. After 24 hours in the presence of growth factors, 10× [$^3$H]thymidine (10 μL/well) is added.

5. Three days after addition of [$^3$H]thymidine, medium is removed by aspiration, and cells are washed twice with Cell Wash Medium (400 μL/well followed by 200 μL/well). The washed, adherent cells are then solubilized by addition of Cell Lysis Solution (100 μL/well) and warming to 37° C. for 30 minutes. Cell lysates are transferred to 7-mL glass scintillation vials containing 150 μL of water. Scintillation cocktail (5 mL/vial) is added, and cell-associated radioactivity is determined by liquid scintillation spectroscopy.

Based upon the foregoing assays the compounds of Formula I are inhibitors of VEGF and thus are useful for the inhibition of angiogenesis, such as in the treatment of ocular disease, e.g., diabetic retinopathy and in the treatment of cancers, e.g., solid tumors. The instant compounds inhibit VEGF-stimulated mitogenesis of human vascular endothelial cells in culture with IC$_{50}$ values between 0.001-5.0 μM. These compounds also show selectivity over related tyrosine kinases (e.g., FGFR1 and the Src family; for relationship between Src kinases and VEGFR kinases, see Eliceiri et al., Molecular Cell, Vol. 4, pp. 915-924, December 1999).

EXAMPLES

Examples provided are intended to assist in a further understanding of the invention. Particular materials employed, species and conditions are intended to be illustrative of the invention and not limiting of the reasonable scope thereof. The compounds of this invention may be prepared by employing reactions as shown in the following schemes, in addition to other standard manipulations that are known in the literature or exemplified in the experimental procedures. These schemes, therefore, are not limited by the compounds listed or by any particular substituents employed for illustrative purposes. Substituent numbering as shown in the schemes does not necessarily correlate to that used in the claims.

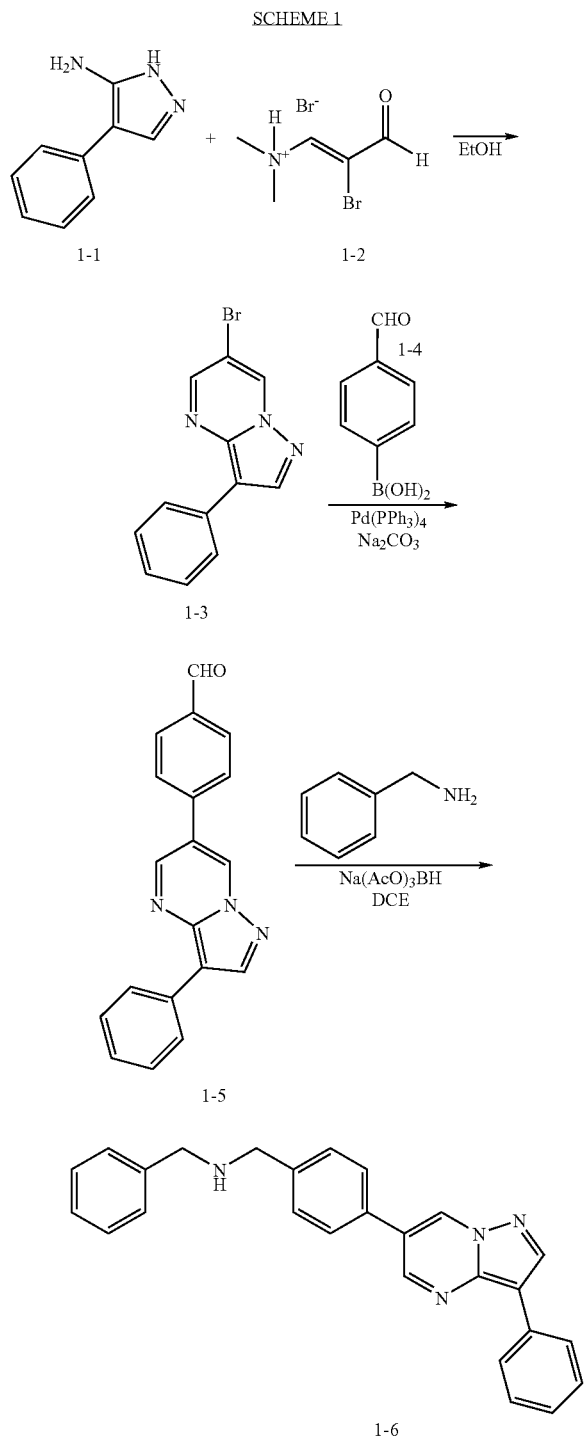

6-bromo-3-phenylpyrazolo[1,5-a]pyrimidine (1-3)

A solution of 3-amino-4-phenylpyrazole (1-1, 5.00 g, 31.6 mmol, 1 equiv) and 2-bromo-3-N,N-dimethylaminoacrolein hydrobromide (1-2, prepared according to literature methods, 9.20 g, 35.5 mmol, 1.12 equiv) in ethanol (120 mL) was heated at reflux for 2 hours. The reaction mixture was allowed to cool to 23° C., and the resulting precipitate was filtered and dried to provide 6-bromo-3-phenylpyrazolo[1,5-a]pyrimidine (1-3) as a white crystalline solid. $^1$H NMR (400 MHz, CDCl$_3$) δ8.83 (d, 1H, J=2.2 Hz), 8.54 (d, 1H, J=2.2 Hz), 8.41 (s, 1H), 8.00 (br d, 2H, J=7.8 Hz), 7.47 (br t, 2H, J=7.7 Hz), 7.31 (t, 1H, J=7.5 Hz).

4-(3-phenylpyrazolo[1,5-a]pyrimidin-6-yl)benzaldehyde (1-5)

A deoxygenated solution of 6-bromo-3-phenylpyrazolo[1,5-a]pyrimidine (1-3, 2.00 g, 7.30 mmol, 1 equiv), 4-formylphenylboronic acid (1-4, 1.65 g, 11.0 mmol, 1.51 equiv), aqueous sodium carbonate solution (6.00 mL, 12.0 mmol, 1.64 equiv), and tetrakis(triphenylphosphine)palladium (0.420 g, 0.363 mmol, 0.0500 equiv) in dioxane (100 mL) was heated at reflux for 20 hours. The reaction mixture was partitioned between aqueous sodium bicarbonate solution (200 mL) and ethyl acetate (200 mL). The organic layer was dried over sodium sulfate and concentrated. The residue was suspended in methanol (100 mL) and filtered to give 4-(3-phenylpyrazolo[1,5-a]pyrimidin-6-yl)benzaldehyde (1-5) as a yellow solid. $^1$H NMR (400 MHz, CDCl$_3$) δ10.11 (s, 1H), 8.93 (d, 1H, J=2.4 Hz), 8.87 (d, 1H, J=2.2 Hz), 8.51 (s, 1H), 8.07 (m, 2H), 7.81 (br d, 2H, J=7.8 Hz), 7.49 (br t, 2H, J=7.7 Hz), 7.32 (t, 1H, J=7.5 Hz).

1-phenyl-N-[4-(3-phenylpyrazolo[1,5-a]pyrimidin-6-yl)benzyl]methanamine (1-6)

A solution of 4-(3-phenylpyrazolo[1,5-a]pyrimidin-6-yl) benzaldehyde (1-5, 75 mg, 0.25 mmol), benzylamine (0.056 mL, 0.50 mmol), acetic acid (14 TL, 0.25 mmol), and sodium triacetoxyborohydride(106 mg, 0.50 mmol) in 1,2-dichloro-ethane (6 mL) was stirred under ambient conditions overnight. The residue was partitioned between sat. NaHCO$_3$ solution (4 mL) and ethyl acetate (3×4 mL). The organic layer was washed with brine and dried over MgSO$_4$ and concentrated. The residue was purified by reverse-phase LC (H$_2$O/CH$_3$CN gradient w/0.1% TFA present) to provide 1-phenyl-N-[4-(3-phenylpyrazolo[1,5-a]pyrimidin-6-yl) benzyl]methanamine (1-6) as a yellow solid. $^1$H NMR (400 MHz, CD$_3$OD) δ9.21 (d, 1H, J=2.4 Hz), 8.96 (d, 1H, J=2.4 Hz), 8.61 (s, 1H), 8.12 (br d, 2H, J=7.8 Hz), 7.91 (d, 2H, J=8.2 Hz), 7.67 (d, 2H, J=7.8 Hz), 7.49 (m, 5H), 7.44 (br t, 2H, J=7.8 Hz), 7.27 (t, 1H, J=7.5 Hz), 4.34 (s, 2H), 4.29 (s, 2H).

The following compounds were prepared by simple modifications of the above procedure.

| Compound | Name | Structure |
|---|---|---|
| 1-7 | N-[4-(3-phenylpyrazolo[1,5-a]pyrimidin-6-yl)benzyl]-N-propylamine | 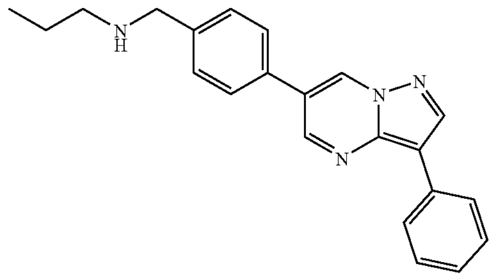 |
| 1-8 | N-(2-methoxyethyl)-N-[4-(3-phenylpyrazolo[1,5-a]pyrimidin-6-yl)benzyl-]butan-1-amine | 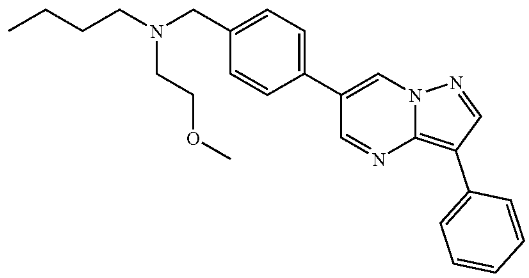 |
| 1-9 | N-[4-(3-phenylpyrazolo[1,5-a]pyrimidin-6-yl)benzyl]cyclopropanamine | 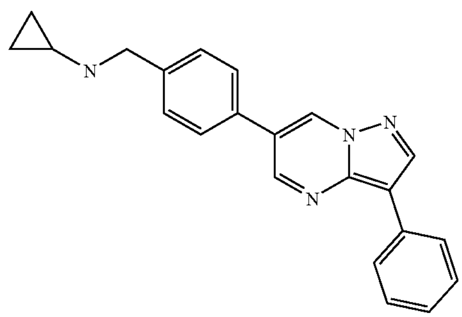 |
| 1-10 | 2-methoxy-N-[4-(3-phenylpyrazolo[1,5-a]pyrimidin-6-yl)benzyl]ethanamine | 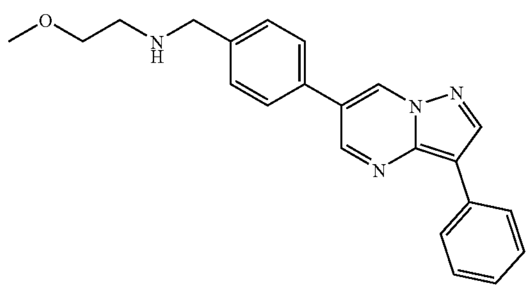 |
| 1-11 | 1-[4-(3-phenylpyrazolo[1,5-a]pyrimidin-6-yl)phenyl]-N-(pyridin-3-ylmethyl)methanamine | 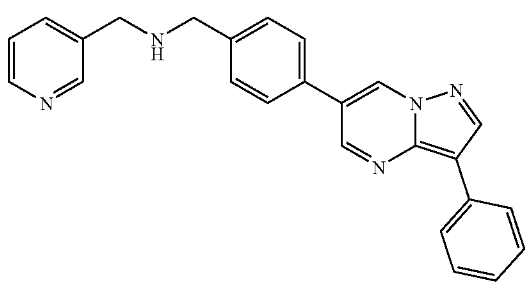 |

-continued

| Compound | Name | Structure |
|---|---|---|
| 1-12 | 1-(3-{[4-(3-phenylpyrazolo[1,5-a]pyrimidin-6-yl)benzyl]amino}propyl)pyrrolidin-2-one | 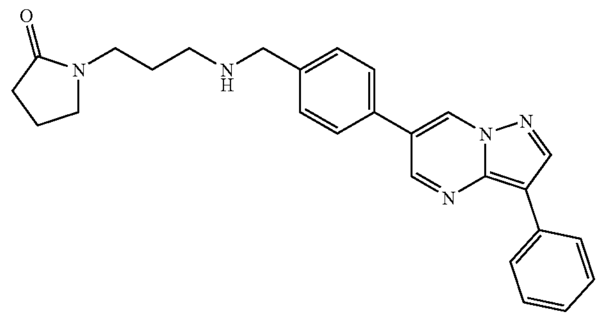 |
| 1-13 | 1-(1-benzylpyrrolidin-3-yl)-N-[4-(3-phenylpyrazolo[1,5-a]pyrimidin-6-yl)benzyl]methanamine | 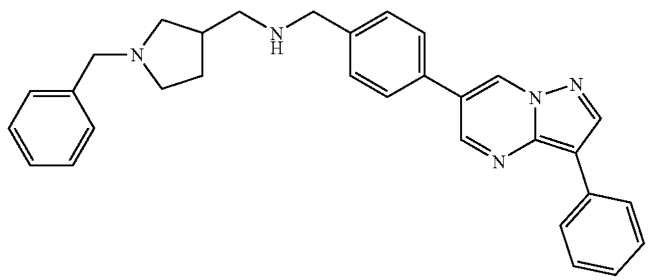 |
| 1-14 | 6-(4-{[4-(methylsulfonyl)piperazin-1-yl]methyl}phenyl)-3-phenylpyrazolo[1,5-a]pyrimidine | 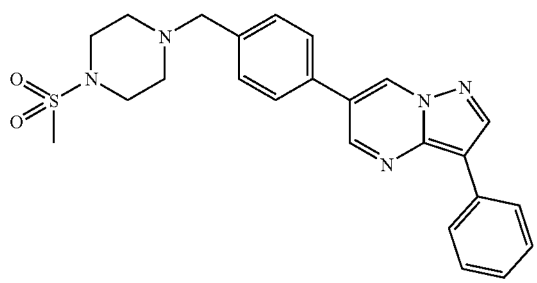 |
| 1-15 | 1-[3-(3-phenylpyrazolo[1,5-a]pyrimidin-6-yl)phenyl]-N-(pyridin-3-ylmethyl)methanamine | 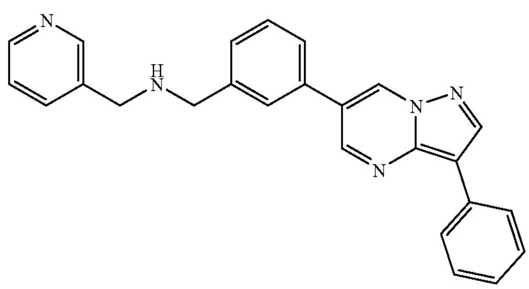 |
| 1-16 | N-3-[3-(3-phenylpyrazolo[1,5-a]pyrimidin-6-yl)benzyl]-beta-alaninamide | 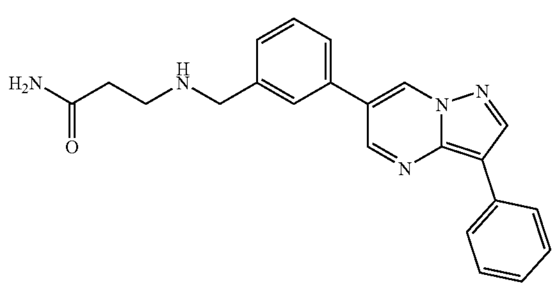 |

-continued
| Compound | Name | Structure |
|---|---|---|
| 1-17 | 1-phenyl-N-[3-(3-phenylpyrazolo[1,5-a]pyrimidin-6-yl)benzyl-]methanamine | 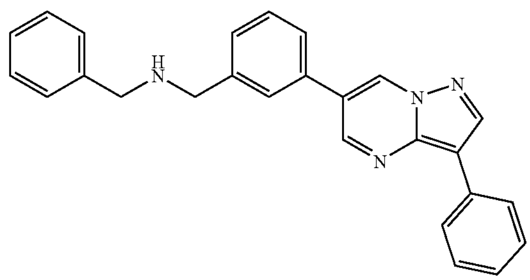 |
| 1-18 | N-[3-(3-phenylpyrazolo[1,5-a]pyrimidin-6-yl)benzyl]-N-propylamine | 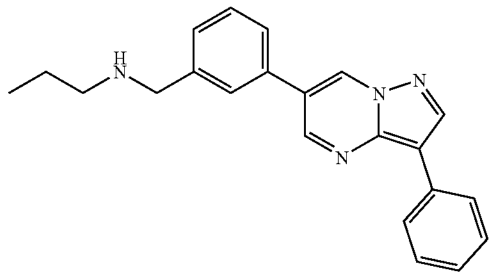 |
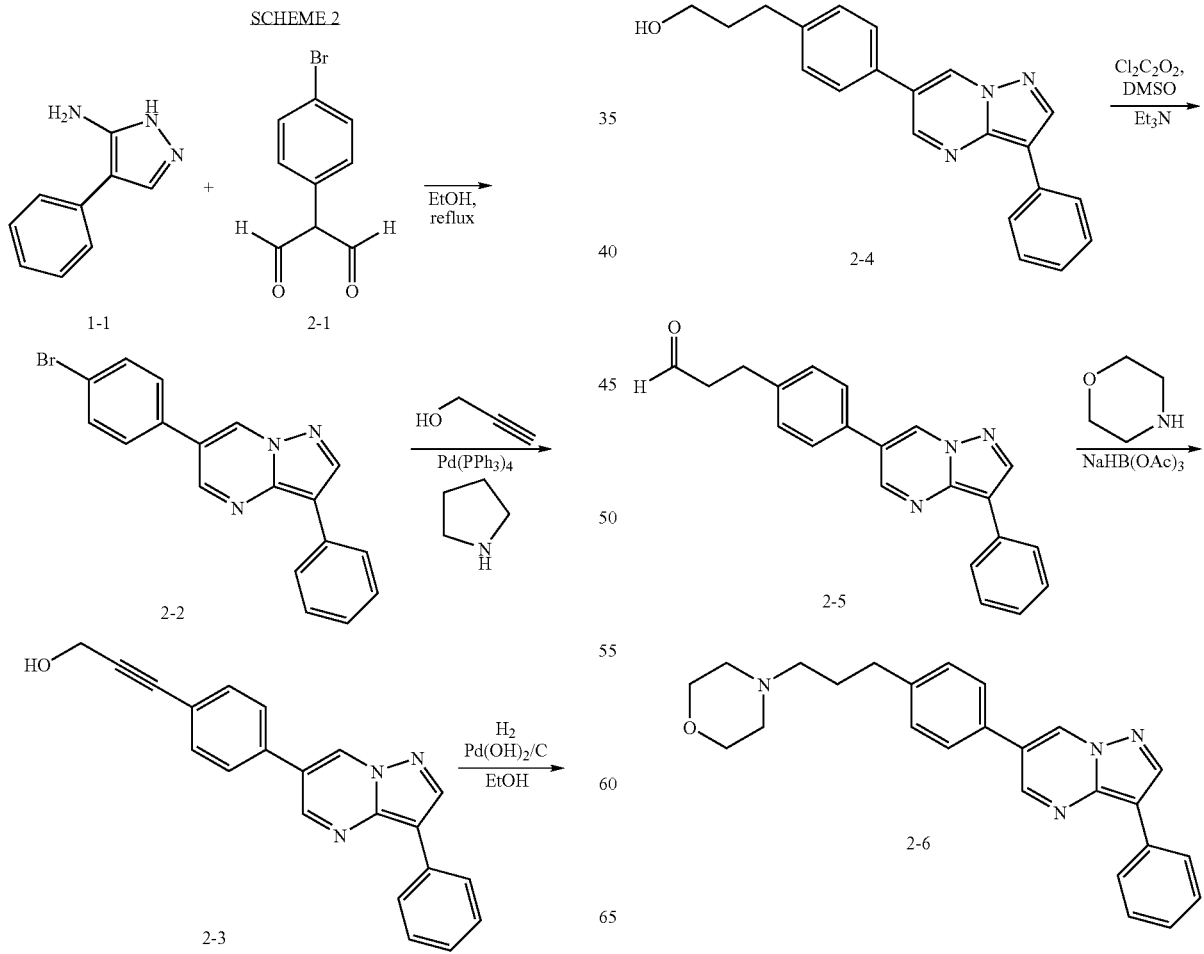

6-(4-bromophenyl)-3-phenylpyrazolo[1,5-a]pyrimidine (2-2)

A solution of 3-aminophenylpyrazole (1-1, 3.26 g, 20.5 mmol, 1 equiv) and 2-(4-bromophenyl)malonaldehyde (2-1, 4.60 g, 20.3 mmol, 1 equiv) in ethanol (100 mL) was heated at reflux for 3 hours. The reaction mixture was allowed to cool to 23° C., and the resulting precipitate filtered and dried to give 6-(4-bromophenyl)-3-phenylpyrazolo[1,5-a]pyrimidine (2-2) as a yellow solid.

3-[4-(3-phenylpyrazolo[1,5-a]pyrimidin-6-yl)phenyl]prop-2-yn-1-ol (2-3)

A deoxygenated mixture of 6-(4-bromophenyl)-3-phenylpyrazolo[1,5-a]pyrimidine (2-2, 3.00 g, 8.57 mmol, 1 equiv), propargyl alcohol (1.50 mL, 25.8 mmol, 3.01 equiv), and tetrakis(triphenylphosphine)palladium (0.500 g, 0.433 mmol, 0.050 equiv) in pyrrolidine (50 mL) was heated at reflux for 2.5 hours. The reaction mixture was concentrated, and the residue was suspended in methanol (50 mL) and filtered to give 3-[4-(3-phenylpyrazolo[1,5-a]pyrimidin-6-yl)phenyl]prop-2-yn-1-ol (2-3) as a yellow solid. $^1$H NMR (400 MHz, DMSO-$d_6$) δ9.56 (d, 1H, J=2.4 Hz), 9.07 (d, 1H, J=2.2 Hz), 8.82 (s, 1H), 8.18 (br d, 2H, J=7.8 Hz), 7.92 (d, 2H, J=8.2 Hz), 7.58 (d, 2H, J=8.2 Hz), 7.46 (t, 2H, J=7.8 Hz), 7.27 (t, 1H, J=7.8 Hz), 5.37 (t, 1H, J=6.0 Hz), 4.35 (d, 2H, J=6.0 Hz).

3-[4-(3-phenylpyrazolo[1,5-a]pyrimidin-6-yl)phenyl]propan-1-ol (2-4)

A mixture of 3-[4-(3-phenylpyrazolo[1,5-a]pyrimidin-6-yl)phenyl]prop-2-yn-1-ol (2-3, 1.48 g, 0.455 mmol) and 10% palladium hydroxide on carbon (2.0 g) in 2-propanol (500 mL) was stirred under a hydrogen balloon for 4.5 hours. The reaction mixture was filtered through celite, and the filtrate was concentrated. The residue was purified by flash column chromatography (chloroform saturated with ammonia gas) to provide 3-[4-(3-phenylpyrazolo[1,5-a]pyrimidin-6-yl)phenyl]propan-1-ol (2-4) as a yellow solid. $^1$H NMR (400 MHz, CDCl$_3$) δ8.83 (s, 2H), 8.46 (s, 1H), 8.07 (br d, 2H, J=7.8 Hz), 7.54 (d, 2H, J=8.2 Hz), 7.47 (t, 2H, J=7.8 Hz), 7.38 (d, 2H, J=8.2 Hz), 7.29 (t, 1H, J=7.8 Hz), 3.73 (q, 2H, J=6.4 Hz), 2.81 (t, 2H, J=7.3 Hz), 1.95 (m, 2H), 1.30 (t, 1H, J=5.3 Hz).

3-[4-(3-phenylpyrazolo[1,5-a]pyrimidin-6-yl)phenyl]propanal (2-5)

Dimethylsulfoxide (0.862 mL, 12.2 mmol, 5.00 equiv) was added to a solution of oxalyl chloride (0.636 mL, 7.29 mmol, 3.00 equiv) in dichloromethane (10 mL) at −78° C. The mixture was stirred for 15 minutes before a solution of 3-[4-(3-phenylpyrazolo[1,5-a]pyrimidin-6-yl)phenyl]propan-1-ol (2-4, 0.800 g, 2.43 mmol, 1 equiv) in dichloromethane (100 mL) was added via cannula over 5 minutes. The resulting mixture was stirred at −78° C. for 1 hour. Triethylamine (3.50 mL, 25.1 mmol, 10.3 equiv) was added, and the mixture was then warmed to 0° C. and stirred for 30 minutes. The reaction mixture was partitioned between saturated sodium bicarbonate solution (100 mL) and additional dichloromethane (100 mL). The organic layer was dried over sodium sulfate and concentrated to give 3-[4-(3-phenylpyrazolo[1,5-a]pyrimidin-6-yl)phenyl]propanal (2-5) as a yellow solid. $^1$H NMR (400 MHz, CDCl$_3$) δ9.86 (t, 1H, J=1.2 Hz), 8.82 (d, 1H, J=2.4 Hz), 8.81 (d, 1H, J=2.4 Hz), 8.46 (s, 1H), 8.06 (br d, 2H, J=7.8 Hz), 7.54 (d, 2H, J=8.2 Hz), 7.47 (t, 2H, J=7.8 Hz), 7.37 (d, 2H, J=8.2 Hz), 7.29 (t, 1H, J=7.8 Hz), 3.05 (t, 2H, J=7.1 Hz), 2.86 (t, 2H, J=7.1 Hz).

6-[4-(3-morpholin-4-ylpropyl)phenyl]-3-phenylpyrazolo[1,5-a]pyrimidine (2-6)

A solution of 3-[4-(3-phenylpyrazolo[1,5-a]pyrimidin-6-yl)phenyl]propanal (2-5, 150 mg, 0.458 mmol, 1 equiv), morpholine (0.048 mL, 0.55 mmol, 1.2 equiv), acetic acid (0.026 mL, 0.55 mmol, 1.0 equiv), and sodium triacetoxyboro-hydride (116 mg, 0.547 mmol, 1.20 equiv) in dichloroethane (8 mL) was stirred in the presence of 4 angstrom molecular sieves for 15 minutes. The reaction mixture was partitioned between saturated sodium bicarbonate solution (100 mL) and ethyl acetate (100 mL). The organic layer was dried over sodium sulfate and concentrated. The residue was purified by flash column chromatography (50% hexane in chloroform saturated with ammonia gas, grading to 100% chloroform saturated with ammonia gas) to give 6-[4-(3-morpholin-4-ylpropyl)phenyl]-3-phenylpyrazolo[1,5-a]pyrimidine (2-6) as a yellow solid (mp=147-149° C.). $^1$H NMR (400 MHz, CDCl$_3$) δ8.82 (s, 2H), 8.45 (s, 1H), 8.06 (br d, 2H, J=7.8 Hz), 7.53 (d, 2H, J=8.2 Hz), 7.47 (t, 2H, J=7.8 Hz), 7.35 (d, 2H, J=8.2 Hz), 7.29 (t, 1H, J=7.8 Hz), 3.73 (m, 4H), 2.73 (t, 2H, J=7.5 Hz), 2.46 (m, 4H), 2.40 (t, 2H, J=7.2 Hz), 1.87 (pentet, 2H, J=7.7 Hz).

The following compounds were prepared by simple modifications of the above procedure.

| Compound | Name | Structure |
|---|---|---|
| 2-7 | 3-phenyl-6-[4-(3-piperidin-1-ylpropyl)phenyl]pyrazolo[1,5-a]pyrimidine | 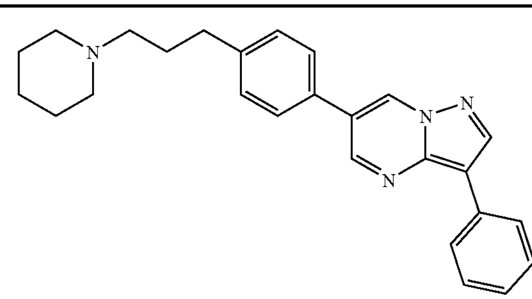 |

-continued
| Compound | Name | Structure |
|---|---|---|
| 2-8 | N-1-ethyl-N-2-dimethyl-N-1-{3-[4-(3-phenylpyrazolo[1,5-a]pyrimidin-6-yl)phenyl]propyl}ethane-1,2-diamine | 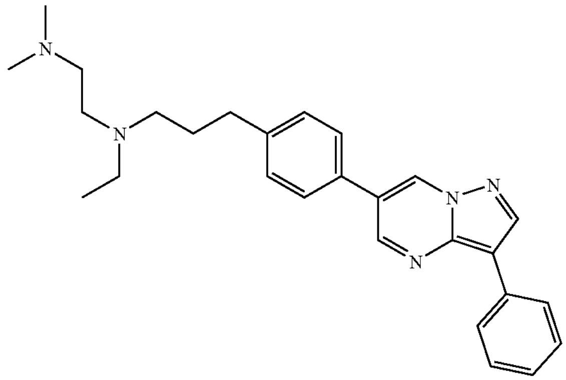 |
| 2-9 | N-[2-(dimethylamino)ethyl]-1-{3-[4-(3-phenylpyrazolo[1,5-a]pyrimidin-6-yl)phenyl]propyl}-D-prolinamide | 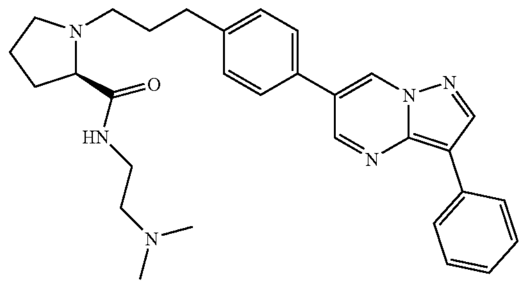 |
| 2-10 | N-[2-(dimethylamino)ethyl]-1-{3-[4-(3-phenylpyrazolo[1,5-a]pyrimidin-6-yl)phenyl]propyl}-L-prolinamide | 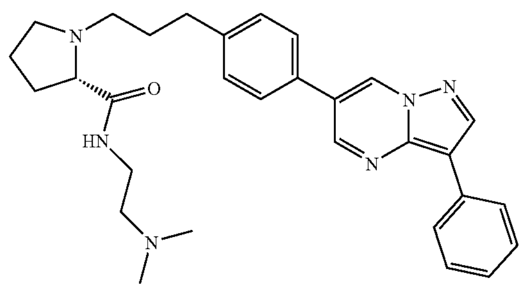 |
-continued
SCHEME 3
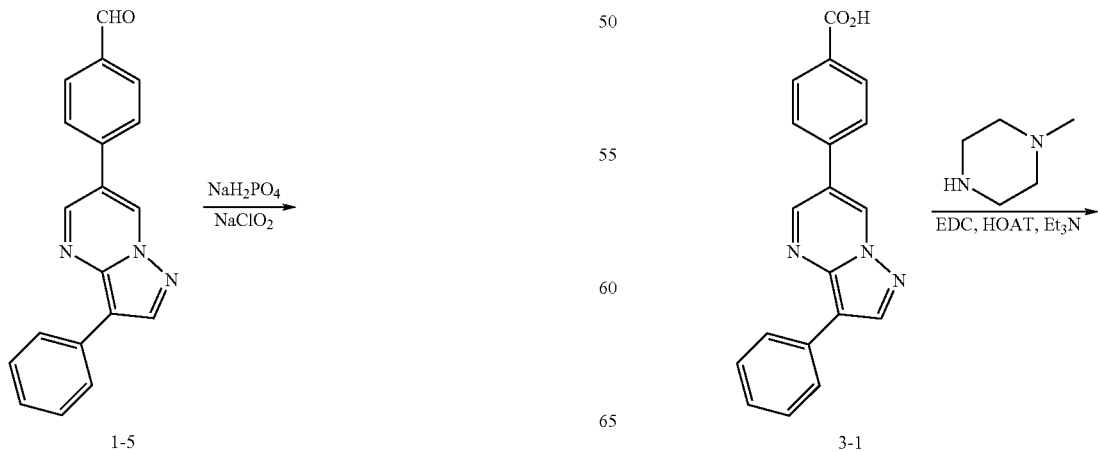

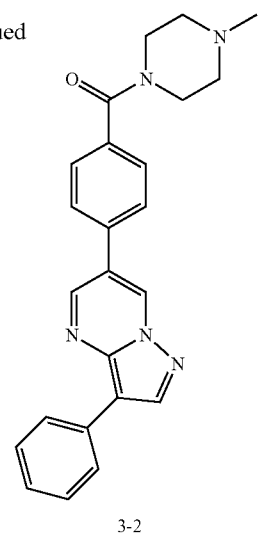

3-2

4-(3-phenylpyrazolo[1,5-a]pyrimidin-6-yl)benzoic acid (3-1)

A solution of 4-(3-phenylpyrazolo[1,5-a]pyrimidin-6-yl)benzaldehyde (1-5, 250 mg, 0.835 mmol, 1 equiv) in a 4:1 mixture of THF and t-BuOH (20 mL) was treated with 2-methyl butene (5 mL), an aqueous solution of sodium phosphate monobasic (0.14 M, 230 mg, 1.67 mmol, 2 equiv) and sodium chlorite (194 mg, 2.15 mmol, 2.57 equiv). After 1 hour at 23° C., additional solid sodium phosphate monobasic (230 mg, 1.67 mmol, 2 equiv) and sodium chlorite (194 mg, 2.15 mmol, 2.57 equiv) were added. The reaction mixture was stirred for an additional 4 hours, concentrated, and the residue dissolved in EtOAc (100 mL) then washed with a 25:1 mixture of aqueous 10% sodium bisulfite solution and 10% potassium hydrogen sulfate solution (2×100 mL). The organic layer was dried over sodium sulfate and concentrated to afford 4-(3-phenylpyrazolo[1,5-a]pyrimidin-6-yl)benzoic acid (3-1) as a yellow solid. LRMS m/z: Calc'd for $C_{19}H_{14}N_3O_2$ (M+H) 316.35, found 316.1.

6-{4-[(4-methylpiperazin-1-yl)carbonyl]phenyl}-3-phenylpyrazolo[1,5-a]pyrimidine (3-2)

A solution of 4-(3-phenylpyrazolo[1,5-a]pyrimidin-6-yl)benzoic acid (3-1, 100 mg, 0.32 mmol, 1 equiv), 1-methyl piperazine (42 μL, 0.38 mmol, 1.20 equiv), 1-(3-dimethylaminopropyl)-3-ethylcarbodiimide hydrochloride (72.9 mg, 0.38 mmol, 1.20 equiv), 1-hydroxy-7-azabenzotriazole (51.8 mg, 0.38 mmol, 1.20 equiv) and triethylamine (110 μL, 0.79 mmol, 2.5 equiv) in DMF (5 mL) was stirred for 18 hours. The solution was partitioned between EtOAc (3×100 mL) and water (150 mL). The combined organic layers were washed with saturated aqueous sodium chloride (150 mL), dried over sodium sulfate, and concentrated. The residue was purified by reverse-phase LC ($H_2O/CH_3CN$ gradient w/0.1% TFA present) to afford 6-{4-[(4-methylpiperazin-1-yl)carbonyl]phenyl}-3-phenylpyrazolo[1,5-a]pyrimidine (3-2) as a TFA salt. $^1$H NMR (500 MHz, DMSO-$d_6$) δ 10.18 (broad s, 1 H), 9.62 (s, 1 H), 9.12 (s, 1 H), 8.84 (s, 1 H), 8.20 (m, 2 H), 8.04 (m, 2 H), 7.64 (m, 2 H), 7.49 (m, 2 H), 7.39 (m, 1 H), 4.81-3.12 (m, 8 H), 2.84 (s, 3H).

The following compounds were made by simple modifications of the above procedures.

| Compound | Name | Structure |
|---|---|---|
| 3-3 | 3-phenyl-6-[4-(piperazin-1-ylcarbonyl)phenyl]pyrazolo[1,5-a]pyrimidine | 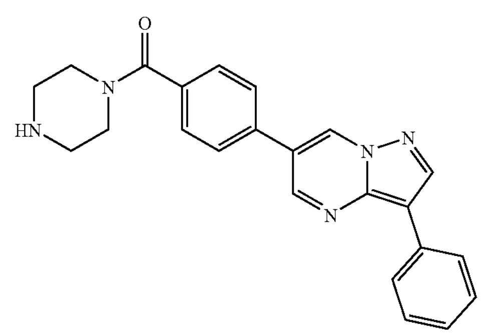 |
| 3-4 | 4-(3-phenylpyrazolo[1,5-a]pyrimidin-6-yl)-N-pyrrolidin-3-ylbenzamide | 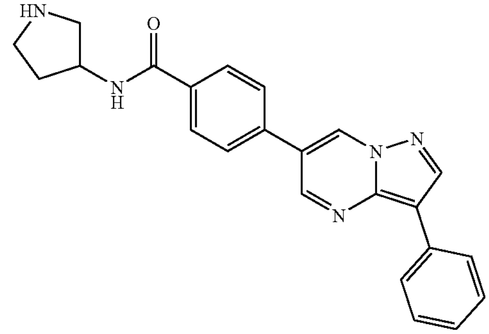 |

SCHEME 4

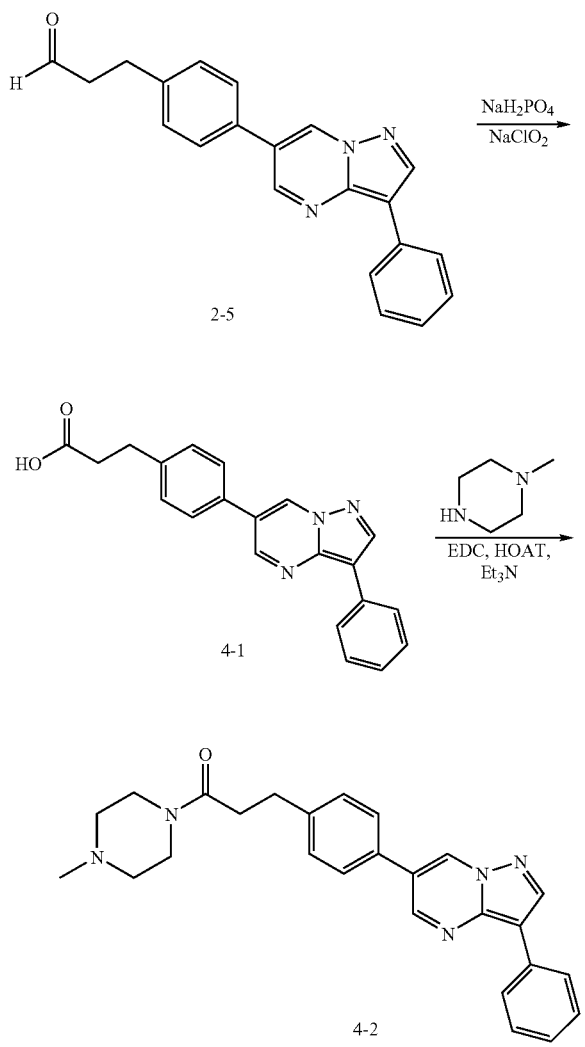

3-[4-(3-phenylpyrazolo[1,5-a]pyrimidin-6-yl)phenyl]propanoic acid (4-1)

A solution of 3-[4-(3-phenylpyrazolo[1,5-a]pyrimidin-6-yl)phenyl]propanal (2-5, 278 mg, 0.850 mmol, 1 equiv) in a 4:1 mixture of THF and t-BuOH (20 mL) was treated with 2-methyl butene (5 mL), an aqueous solution of sodium phosphate monobasic (0.14 M, 234 mg, 1.70 mmol, 2 equiv) and sodium chlorite (197 mg, 2.18 mmol, 2.57 equiv). After 1 hour at room temperature, additional solid sodium phosphate monobasic (278 mg, 1.70 mmol, 2 equiv) and sodium chlorite (197 mg, 2.18 mmol, 2.57 equiv) were added. The reaction mixture was stirred for an additional 4 hours, concentrated and the residue dissolved in EtOAc (100 mL) then washed with a 25:1 mixture of aqueous 10% sodium bisulfite solution and 10% potassium hydrogen sulfate solution (2×100 mL). The organic layer was dried over sodium sulfate and concentrated to afford 3-[4-(3-phenylpyrazolo[1,5-a]pyrimidin-6-yl)phenyl]propanoic acid (4-1) as a yellow solid. LRMS m/z: Calc'd for $C_{21}H_{18}N_3O_2$ (M+H) 344.4, found 344.1.

6-{4-[3-(4-methylpiperazin-1-yl)-3-oxopropyl]phenyl}-3-phenylpyrazolo[1,5-a]pyrimidine (4-2)

A solution of 3-[4-(3-phenylpyrazolo[1,5-a]pyrimidin-6-yl)phenyl]propanoic acid (41, 105 mg, 0.31 mmol, 1 equiv), 1-methyl piperazine (40 µL, 0.37 mmol, 1.20 equiv), 1-(3-dimethylaminopropyl)-3-ethylcarbodiimide hydrochloride (70.3 mg, 0.37 mmol, 1.20 equiv), 1-hydroxy-7-azabenzotriazole (49.9 mg, 0.37 mmol, 1.20 equiv) and triethylamine (106 µL, 0.76 mmol, 2.5 equiv) in DMF (5 mL) was stirred for 18 hours. The solution was partitioned between EtOAc (3×100 mL) and water (150 mL). The combined organic layers were washed with saturated aqueous sodium chloride (150 mL), dried over sodium sulfate, and concentrated. The residue was purified by reverse-phase LC ($H_2O/CH_3CN$ gradient w/0.1% TFA present) to afford 6-{4-[3-(4-methylpiperazin-1-yl)-3-oxopropyl]phenyl}-3-phenylpyrazolo[1,5-a]pyrimidine (4-2) as a TFA salt. $^1$H NMR (500 MHz, DMSO-$d_6$) δ 9.96 (broad s, 1 H), 9.51 (s, 1 H), 9.06 (s, 1 H), 8.81 (s, 1 H), 8.28 (m, 2 H), 8.81 (m, 2 H), 7.44 (m, 4 H), 7.27 (m, 1 H), 4.61-2.79 (m, 12 H), 2.76 (s, 3 H).

The following compounds were made by simple modifications of the above procedures.

| Compound | Name | Structure |
|---|---|---|
| 4-3 | 6-[4-(3-oxo-3-piperazin-1-ylpropyl)phenyl]-3-phenylpyrazolo[1,5-a]pyrimidine | 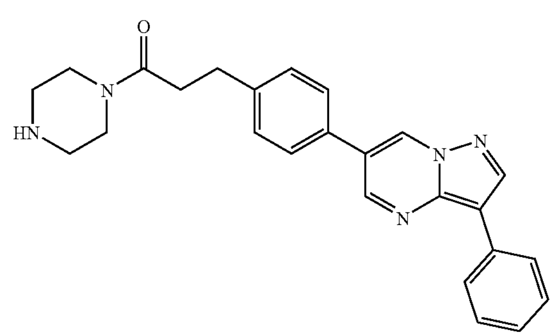 |

| Compound | Name | Structure |
|---|---|---|
| 4-4 | 3-[4-(3-phenylpyrazolo[1,5-a]pyrimidin-6-yl)phenyl]-N-pyrrolidin-3-ylpropanamide | 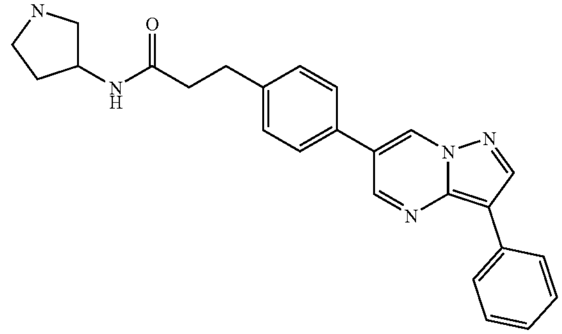 |
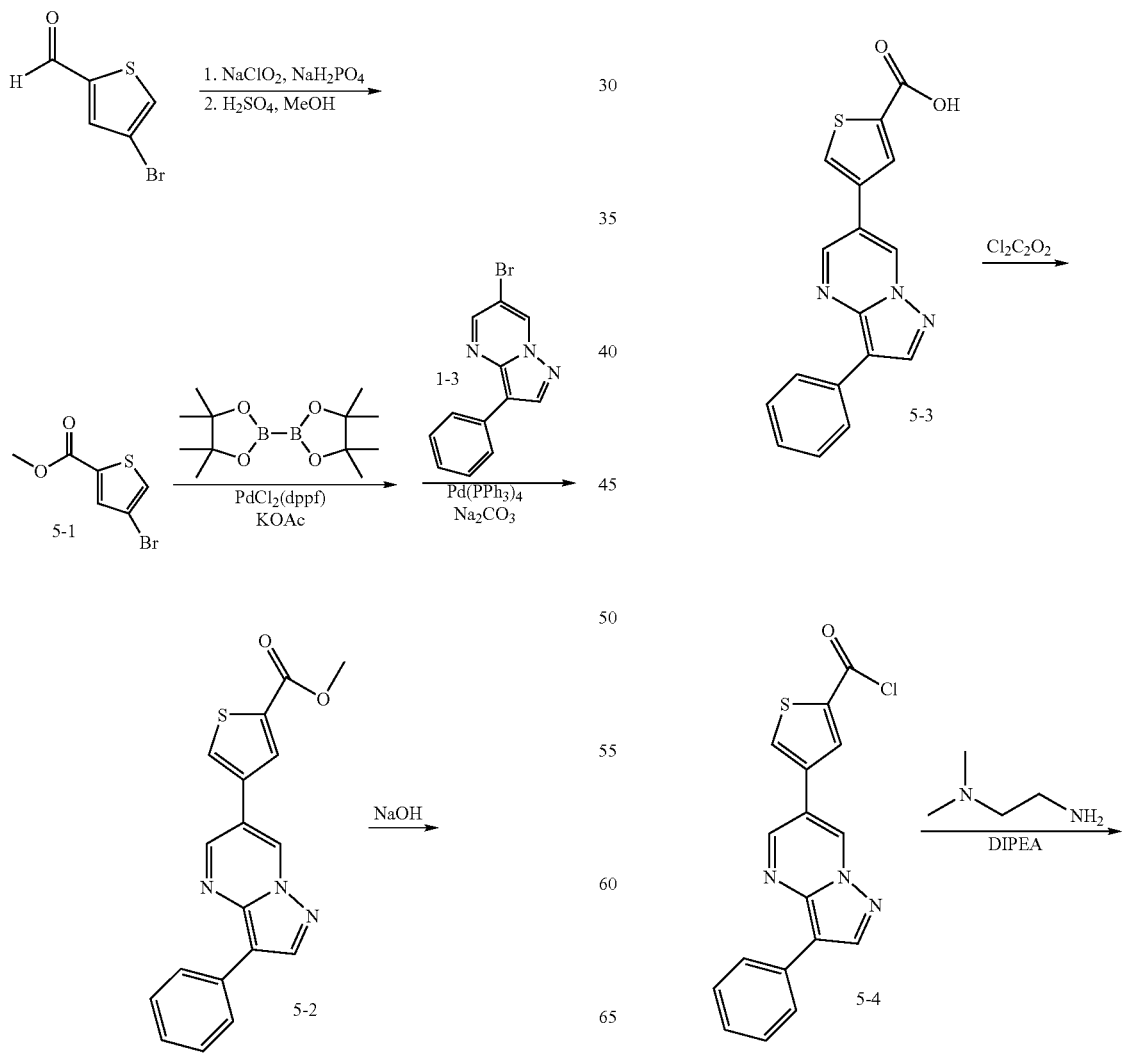

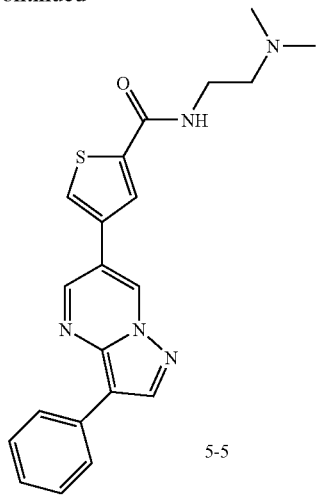

5-5

Methyl 4-bromothiophene-2-carboxylate (5-1)

A biphasic mixture of 4-bromothiophene-2-carbaldehyde (13.2 g, 69.1 mmol, 1 equiv), sodium chlorite (9.40 g, 104 mmol, 1.50 equiv), sodium phosphate monobasic (9.53 g, 69.1 mmol, 1.00 equiv) in a mixture of t-BuOH (120 mL), 2-methyl-2-butene (20 mL), and water (50 mL) was stirred at 23° C. for 1 hour. More sodium chlorite 3.00 g, 33.2 mmol, 0.480 equiv) and a solution of sodium phosphate monobasic (3.00 g, 21.7 mmol, 0.315 equiv) in water (25 mL) were added. The resulting mixture was stirred for 1 hour, then concentrated. The residue was diluted with aqueous 0.1 N sodium hydroxide solution, and the resulting aqueous mixture was extracted with ethyl acetate (200 mL). The aqueous layer was then acidified to pH 2 with aqueous 1 N HCl solution and extracted with dichloromethane (3×100 mL). The organic layer was dried over sodium sulfate and concentrated. The residue was dissolved in anhydrous methanol (600 mL) and concentrated sulfuric acid (4 mL) was added. The resulting solution was heated at reflux for 48 hours. The reaction mixture was concentrated, then carefully partitioned between aqueous saturated sodium bicarbonate solution (400 mL) and ethyl acetate (2×200 mL). The organic layer was dried over sodium sulfate and concentrated to give methyl 4-bromothiophene-2-carboxylate (5-1) as a colorless oil. $^1$H NMR (400 MHz, CDCl$_3$) δ 7.69 (d, 1H, J=1.5 Hz), 7.44 (d, 1H, J=1.5 Hz), 3.90 (s, 3H).

Methyl 4-(3-phenylpyrazolo[1,5-a]pyrimidin-6-yl) thiophene-2-carboxylate (5-2)

A mixture of methyl 4-(4,4,5,5-tetramethyl-1,3,2-dioxaborolan-2-yl)thiophene-2-carboxylate (5-1, 3.00 g, 13.6 mmol, 1 equiv), 4,4,4',4',5,5,5',5'-octamethyl-2,2'-bi-1,3,2-dioxaborolane (3.80 g, 15.0 mmol, 1.10 equiv), potassium acetate (4.10 g, 41.8 mmol, 3.07 equiv), and 1,1'-bis(diphenylphophino)-ferrocene)dichloropalladium (360 mg, 0.44 mmol, 0.032 equiv) in DMF (50 mL) was heated at 80° C. for 4 hours. The reaction mixture was concentrated and the residue was partitioned between aqueous half-saturated sodium bicarbonate solution and ethyl acetate (150 mL). The organic layer was dried over sodium sulfate and concentrated. A solution of this residue, 6-bromo-3-phenylpyrazolo[1,5-a]pyrimidine (1-3, 1.90 g, 6.93 mmol, 0.510 equiv), and tetrakis(triphenylphosphine)palladium (400 mg, 0.350 mmol, 0.025 equiv) in a mixture of dioxane and aqueous sodium carbonate solution (2M, 7 mL, 14 mmol, 1.0 equiv) was heated at reflux for 20 hours. The reaction mixture was partitioned between aqueous saturated sodium bicarbonate solution and ethyl acetate. The organic layer was dried over sodium sulfate and concentrated. The residue was suspended in methanol and filtered to give methyl 4-(3-phenylpyrazolo[1,5-a]pyrimidin-6-yl)thiophene-2-carboxylate (5-2) as a yellow solid. $^1$H NMR (400 MHz, CDCl$_3$) δ 8.86 (d, 1H, J=2.4 Hz), 8.80 (d, 1H, J=2.2 Hz), 8.46 (s, 1H), 8.07 (d, 1H, J=1.6 Hz), 8.05 (br d, 2H, J=7.8 Hz), 7.75 (d, 1H, J=1.6 Hz), 7.47 (br t, 2H, J=7.7 Hz), 7.30 (t, 1H, J=7.5 Hz), 3.95 (s, 3H).

4-(3-phenylpyrazolo[1,5-a]pyrimidin-6-yl) thiophene-2-carboxylic acid (5-3)

A solution of methyl 4-(3-phenylpyrazolo[1,5-a]pyrimidin-6-yl)thiophene-2-carboxylate (5-2, 2.0 g, 6.0 mmol, 1 equiv) in a mixture of aqueous sodium hydroxide solution (1N, 18 mL, 18 mmol, 3.0 equiv) and n-BuOH (100 mL) was heated at reflux for 1 hour. The reaction mixture was concentrated, and the residue was suspended in aqueous 1 N hydrogen chloride solution (100 mL) and filtered. The filtered solid was washed with water and dried to give 4-(3-phenylpyrazolo[1,5-a]pyrimidin-6-yl)thiophene-2-carboxylic acid (5-3). $^1$H NMR (400 MHz, DMSO-d$_6$) δ 9.68 (d, 1H, J=2.4 Hz), 9.15 (d, 1H, J=2.2 Hz), 8.79 (s, 1H), 8.48 (d, 1H, J=1.6 Hz), 8.41 (d, 1H, J=1.6 Hz), 8.16 (br d, 1H, J=7.8 Hz), 7.46 (br t, 2H, J=7.8 Hz), 7.26 (t, 1H, J=7.5 Hz).

4-(3-phenylpyrazolo[1,5-a]pyrimidin-6-yl) thiophene-2-carbonyl chloride (5-4)

A solution of 4-(3-phenylpyrazolo[1,5-a]pyrimidin-6-yl)thiophene-2-carboxylic acid (5-3, 1.0 g, 3.11 mmol, 1 equiv) and oxalyl chloride (2.17 mL, 24.9 mmol, 8.00 equiv) in dichloromethane (400 mL) was stirred at 23° C. for 72 hours. The reaction mixture was concentrated to give 4-(3-phenylpyrazolo[1,5-a]pyrimidin-6-yl)thiophene-2-carbonyl chloride (5-4) as a yellow solid. $^1$H NMR (400 MHz, CDCl$_3$) δ 8.89 (d, 1H, J=2.4 Hz), 8.79 (d, 1H, J=2.2 Hz), 8.50 (s, 1H), 8.22 (d, 1H, J=1.6 Hz), 8.05 (br d, 2H, J=7.8 Hz), 8.00 (d, 1H, J=1.6 Hz), 7.48 (br t, 2H, J=7.7 Hz), 7.31 (t, 1H, J=7.5 Hz).

N-[2-(dimethylamino)ethyl]-4-(3-phenylpyrazolo[1,5-a]pyrimidin-6-yl)thiophene-2-carboxamide (5-5)

A solution of 4-(3-phenylpyrazolo[1,5-a]pyrimidin-6-yl)thiophene-2-carbonyl chloride (5-4, 5.0 mg, 0.015 mmol, 1 equiv), diisopropylethylamine (60 TL, 0.030 mmol, 2.0 equiv), and N,N-dimethylethane-1,2-diamine (41 TL, 0.016 mmol, 1.1 equiv) in dichloromethane (1 mL) was mixed and allowed to stand for 8 hours. The reaction mixture was washed with aqueous half-saturated sodium bicarbonate solution (0.5 mL). The organic layer was dried over sodium sulfate and concentrated to give N-[2-(dimethylamino)ethyl]-4-(3-phenylpyrazolo[1,5-a]pyrimidin-6-yl)thiophene-2-carboxamide (5-5) as a yellow solid. LRMS m/z: Calc'd for $C_{21}H_{22}N_5OS$ (M+H) 392.2, found 392.3.

The following compounds were prepared by simple modifications of the above procedure.

| Compound | Name | Structure |
|---|---|---|
| 5-6 | 4-(3-phenylpyrazolo[1,5-a]pyrimidin-6-yl)-N-(pyridin-3-ylmethyl)thiophene-2-carboxamide | 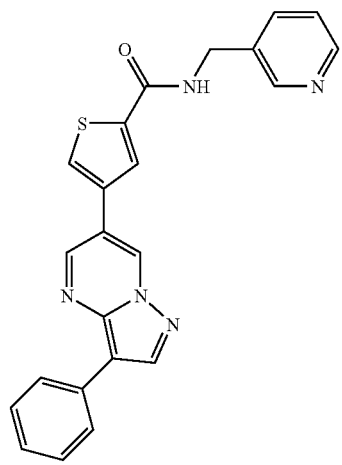 |
| 5-7 | N-(2-methoxyethyl)-4-(3-phenylpyrazolo[1,5-a]pyrimidin-6-yl)thiophene-2-carboxamide | 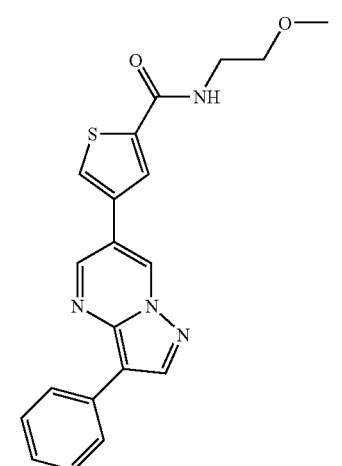 |
| 5-8 | N-(3-morpholin-4-ylpropyl)-4-(3-phenylpyrazolo[1,5-a]pyrimidin-6-yl)thiophene-2-carboxamide | 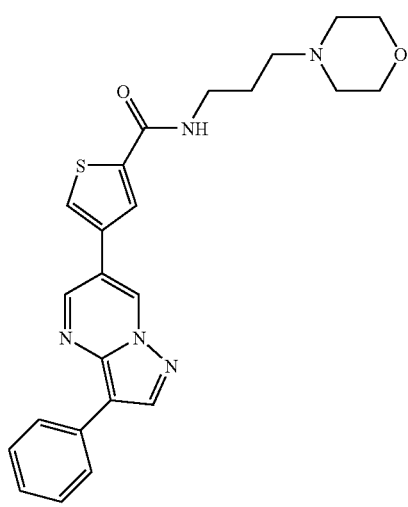 |

| Compound | Name | Structure |
|---|---|---|
| 5-9 | N-[3-(dimethylamino)-2,2-dimethylpropyl]-4-(3-phenylpyrazolo[1,5-a]pyrimidin-6-yl)thiophene-2-carboxamide | 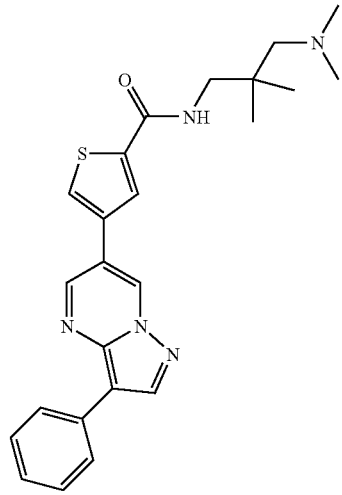 |
| 5-10 | N-[2-(diethylamino)ethyl]-4-(3-phenylpyrazolo[1,5-a]pyrimidin-6-yl)thiophene-2-carboxamide | 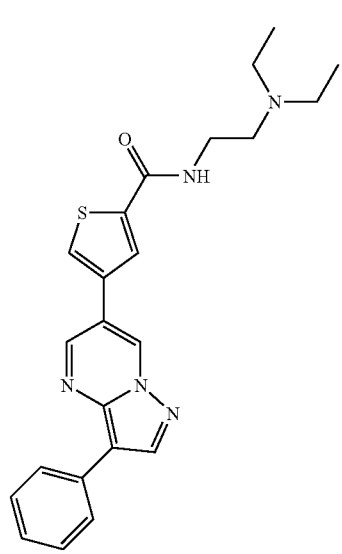 |
| 5-11 | N-[3-(1H-imidazol-1-yl)propyl]4-(3-phenylpyrazolo[1,5-a]pyrimidin-6-yl)thiophene-2-carboxamide | 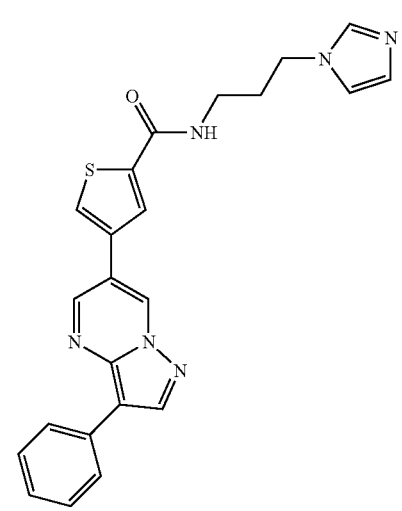 |

-continued
| Compound | Name | Structure |
|---|---|---|
| 5-12 | 4-(3-phenylpyrazolo[1,5-a]pyrimidin-6-yl)-N-(2-pyridin-3-ylethyl)thiophene-2-carboxamide | 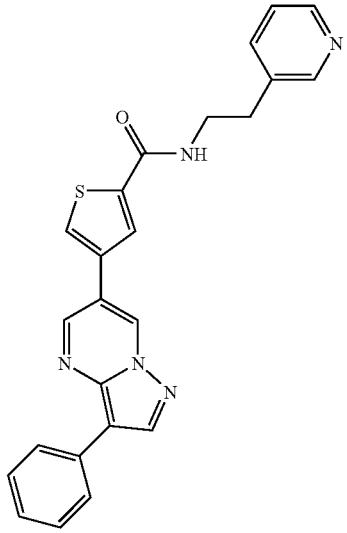 |
| 5-13 | N-[2-(1-methylpyrrolidin-2-yl)ethyl]-4-(3-phenylpyrazolo[1,5-a]pyrimidin-6-yl)thiophene-2-carboxamide | 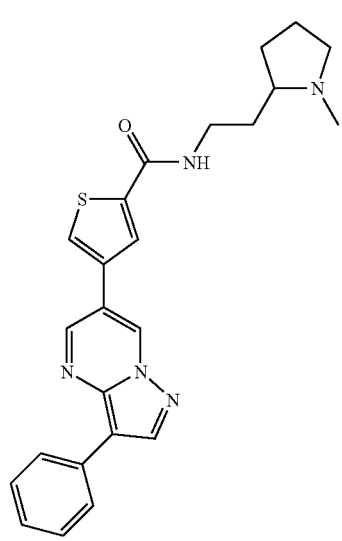 |
| 5-14 | N-[(1-ethylpyrrolidin-3-yl)methyl]-4-(3-phenylpyrazolo[1,5-a]pyrimidin-6-yl)thiophene-2-carboxamide | 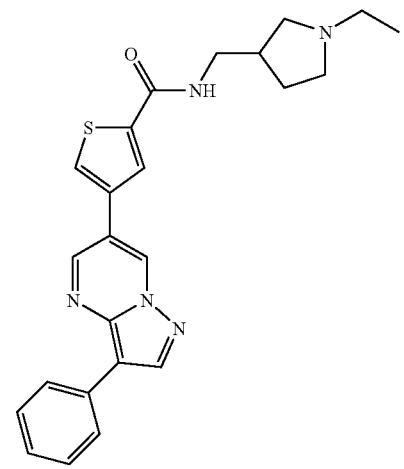 |

SCHEME 6

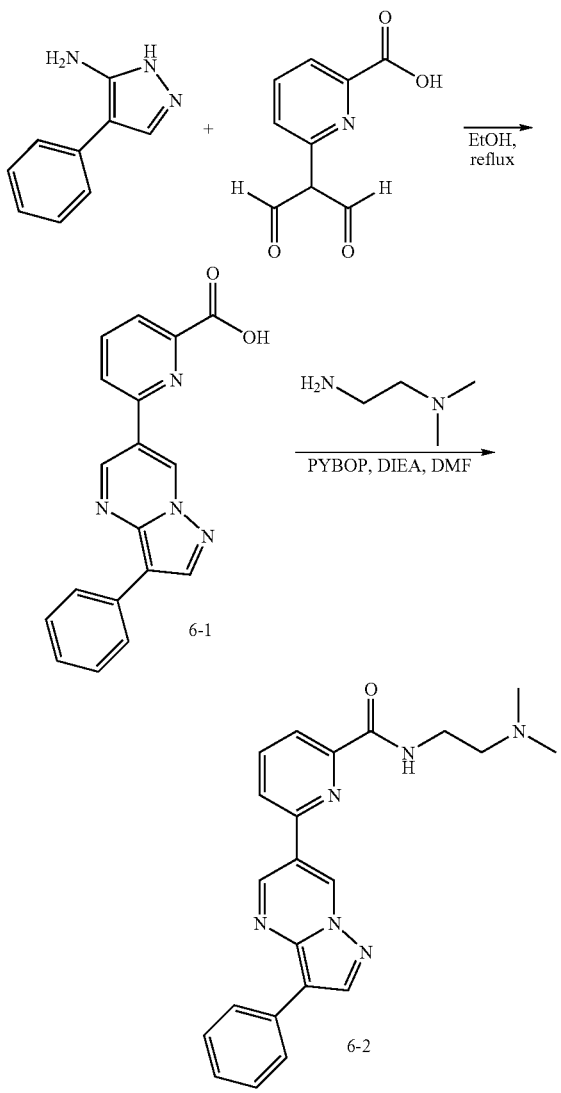

6-(3-phenylpyrazolo[1,5-a]pyrimidin-6-yl)pyridine-2-carboxylic acid (6-1)

A solution 3-amino-4-phenylpyrazole (200 mg, 1.26 mmol, 1 equiv) and 2-(2-hydroxycarbonyl-6-pyridylmalondialdehyde (243 mg, 1.26 mmol, 1 equiv) in ethanol (25 mL) was heated to reflux for 3 hours. The reaction mixture was cooled to 23° C., and the resulting precipitate filtered and dried to give 6-(3-phenylpyrazolo[1,5-a]pyrimidin-6-yl)pyridine-2-carboxylic acid (6-1) as a yellow solid. $^1$H NMR (500 MHz, DMSO-$d_6$) δ 13.23 (s, 1 H), 10.60 (d, 1 H, J=1.9 Hz), 9.50 (d, 1 H, J=2.2 Hz), 8.89 (s, 1 H), 8.46 (d, 1 H, J=7.8 Hz), 8.18 (m, 3 H), 8.08 (d, 1 H, J=7.6 Hz), 7.48 (t, 2H, J=7.5 Hz), 7.28 (t, 1 H, J=7.3 Hz).

N-[2-(dimethylamino)ethyl]-6-(3-phenylpyrazolo[1,5-a]pyrimidin-6-yl)pyridine-2-carboxamide (6-2)

A solution of 6-(3-phenylpyrazolo[1,5-a]pyrimidin-6-yl)pyridine-2-carboxylic acid (6-1, 100 mg, 0.32 mmol, 1 equiv), benzotriazole-1-yl-oxy-trispyrrolidinophosphonium hexafluorophosphate (197 mg, 0.73 mmol, 1.2 equiv), N,N-dimethylethylenediamine (70 µL, 0.63 mmol, 2 equiv) and N,N-diisopropylethyl-amine (20 µL, 0.73 mmol, 2.3 equiv) in DMF (5 mL) was stirred at 23° C. for 3 hours. The solution was partitioned between EtOAc (3×100 mL) and water (120 mL). The combined organic layers were washed with brine (200 mL), dried over sodium sulfate, then concentrated to afford N-[2-(dimethylamino)ethyl]-6-(3-phenylpyrazolo[1,5-a]pyrimidin-6-yl)pyridine-2-carboxamide (6-2). $^1$H NMR (500 MHz, DMSO-$d_6$) δ 10.21 (s, 1 H), 9.72 (s, 1 H), 9.42 (m, 1 H), 8.91 (s, 1 H), 8.47 (m, 1 H), 8.08 (m, 3 H), 7.48 (m, 2 H), 7.29 (m, 1 H), 3.73 (m, 2 H), 3.36 (m, 2 H), 2.89 (s, 3 H), 1.74 (s, 3 H).

The following compound was also made by simple modifications of the above procedures.

| Compound | Name | Structure |
|---|---|---|
| 6-3 | N-(2-aminoethyl)-6-(3-phenylpyrazolo[1,5-a]pyrimidin-6-yl)pyridine-2-carboxamide | 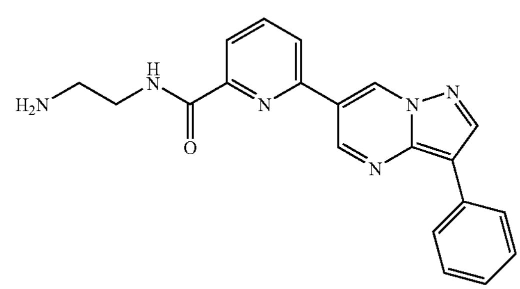 |

What is claimed is:

1. A compound selected from:
1-phenyl-N-[4-(3-phenylpyrazolo[1,5-a]pyrimidin-6-yl)benzyl]methanamine;
N-[4-(3-phenylpyrazolo[1,5-a]pyrimidin-6-yl)benzyl]-N-propylamine;
N-(2-methoxyethyl)-N-[4-(3-phenylpyrazolo[1,5-a]pyrimidin-6-yl)benzyl]butan-1-amine;
N-[4-(3-phenylpyrazolo[1,5-a]pyrimidin-6-yl)benzyl]cyclopropanamine;
2-methoxy-N-[4-(3-phenylpyrazolo[1,5-a]pyrimidin-6-yl)benzyl]ethanamine;
1-[4-(3-phenylpyrazolo[1,5-a]pyrimidin-6-yl)phenyl]-N-(pyridin-3-ylmethyl)methanamine;
1-(3-{[4-(3-phenylpyrazolo[1,5-a]pyrimidin-6-yl)benzyl]amino}propyl)pyrrolidin-2-one;
1-(1-benzylpyrrolidin-3-yl)-N-[4-(3-phenylpyrazolo[1,5-a]pyrimidin-6-yl)benzyl]methanamine;
6-(4-{[4-(methylsulfonyl)piperazin-1-yl]methyl}phenyl)-3-phenylpyrazolo[1,5-a]pyrimidine;
1-[3-(3-phenylpyrazolo[1,5-a]pyrimidin-6-yl)phenyl]-N-(pyridin-3-ylmethyl)methanamine;
N-3-[3-(3-phenylpyrazolo[1,5-a]pyrimidin-6-yl)benzyl]-beta-alaninamide;
1-phenyl-N-[3-(3-phenylpyrazolo[1,5-a]pyrimidin-6-yl)benzyl]methanamine;
N-[3-(3-phenylpyrazolo[1,5-a]pyrimidin-6-yl)benzyl]-N-propylamine;
6-[4-(3-morpholin-4-ylpropyl)phenyl]-3-phenylpyrazolo[1,5-a]pyrimidine;
3-phenyl-6-[4-(3-piperidin-1-ylpropyl)phenyl]pyrazolo[1,5-a]pyrimidine;
N-1-ethyl-N-2-dimethyl-N-1-{3-[4-(3-phenylpyrazolo[1,5-a]pyrimidin-6-yl)phenyl]propyl}ethane-1,2-diamine;
N-[2-(dimethylamino)ethyl]-1-{3-[4-(3-phenylpyrazolo[1,5-a]pyrimidin-6-yl)phenyl]propyl}-D-prolinamide;
N-[2-(dimethylamino)ethyl]-1-{3-[4-(3-phenylpyrazolo[1,5-a]pyrimidin-6-yl)phenyl]propyl}-L-prolinamide;
6-{4-[(4-methylpiperazin-1-yl)carbonyl]phenyl}-3-phenylpyrazolo[1,5-a]pyrimidine;
3-phenyl-6-[4-(piperazin-1-ylcarbonyl)phenyl]pyrazolo[1,5-a]pyrimidine;
4-(3-phenylpyrazolo[1,5-a]pyrimidin-6-yl)-N-pyrrolidin-3-ylbenzamide;
6-{4-[3-(4-methylpiperazin-1-yl)-3-oxopropyl]phenyl}-3-phenylpyrazolo[1,5-a]pyrimidine;
6-[4-(3-oxo-3-piperazin-1-ylpropyl)phenyl]-3-phenylpyrazolo[1,5-a]pyrimidine;
3-[4-(3-phenylpyrazolo[1,5-a]pyrimidin-6-yl)phenyl]-N-pyrrolidin-3-ylpropanamide;
N-[2-(dimethylamino)ethyl]-4-(3-phenylpyrazolo[1,5-a]pyrimidin-6-yl)thiophene-2-carboxamide;
4-(3-phenylpyrazolo[1,5-a]pyrimidin-6-yl)-N-(pyridin-3-ylmethyl)thiophene-2-carboxamide;
N-(2-methoxyethyl)-4-(3-phenylpyrazolo[1,5-a]pyrimidin-6-yl)thiophene-2-carboxamide;
N-(3-morpholin-4-ylpropyl)-4-(3-phenylpyrazolo[1,5-a]pyrimidin-6-yl)thiophene-2-carboxamide;
N-[3-(dimethylamino)-2,2-dimethylpropyl]-4-(3-phenylpyrazolo[1,5-a]pyrimidin-6-yl)thiophene-2-carboxamide;
N-[2-(diethylamino)ethyl]-4-(3-phenylpyrazolo[1,5-a]pyrimidin-6-yl)thiophene-2-carboxamide;
N-[3-(1H-imidazol-1-yl)propyl]-4-(3-phenylpyrazolo[1,5-a]pyrimidin-6-yl)thiophene-2-carboxamide;
4-(3-phenylpyrazolo[1,5-a]pyrimidin-6-yl)-N-(2-pyridin-3-ylethyl)thiophene-2
N-[2-(1-methylpyrrolidin-2-yl)ethyl]-4-(3-phenylpyrazolo[1,5-a]pyrimidin-6-yl)thiophene-2-carboxamide;
N-[(1-ethylpyrrolidin-3-yl)methyl]-4-(3-phenylpyrazolo[1,5-a]pyrimidin-6-yl)thiophene-2-carboxamide;
N-[2-(dimethylamino)ethyl]-6-(3-phenylpyrazolo[1,5-a]pyrimidin-6-yl)pyridine-2-carboxamide; and
N-(2-aminoethyl)-6-(3-phenylpyrazolo[1,5-a]pyrimidin-6-yl)pyridine-2-carboxamide;

or a pharmaceutically acceptable salt or stereoisomer thereof.

2. The compound according to claim 1 which is 6-[4-(3-morpholin-4-ylpropyl)phenyl]-3-phenylpyrazolo[1,5-a]pyrimidine

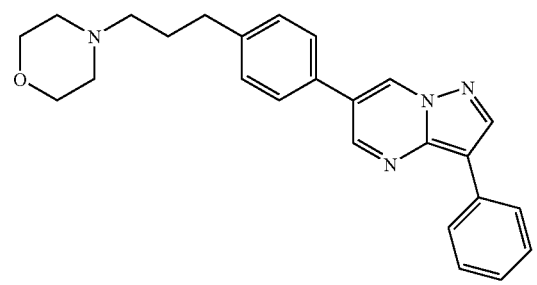

or a pharmaceutically acceptable salt or stereoisomer thereof.

3. The compound according to claim 1 which is 3-phenyl-6-[4-(3-piperidin-1-ylpropyl)phenyl]pyrazolo[1,5-a]pyrimidine

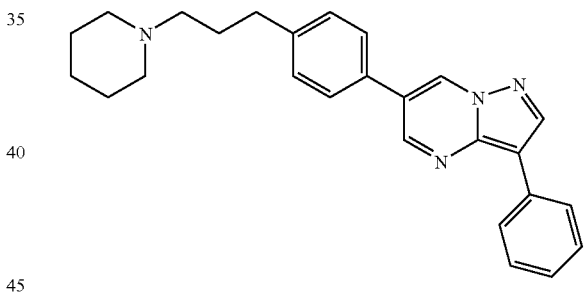

or a pharmaceutically acceptable salt or stereoisomer thereof.

4. The compound according to claim 1 which is 6-{4-[3-(4-methylpiperazin-1-yl)-3-oxopropyl]phenyl}-3-phenylpyrazolo[1,5-a]pyrimidine

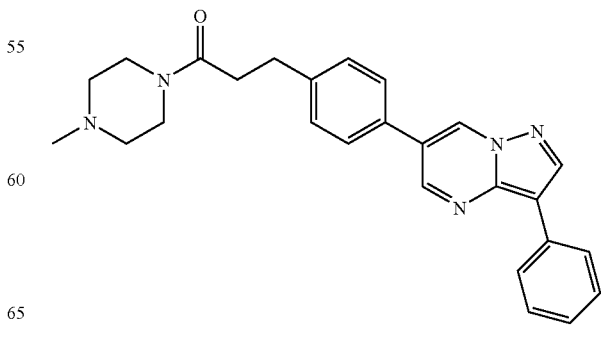

or a pharmaceutically acceptable salt or stereoisomer thereof.

5. The compound according to claim 1 which is 6-{4-[(4-methylpiperazin-1-yl)carbonyl]phenyl}-3-phenylpyrazolo[1,5-a]pyrimidine

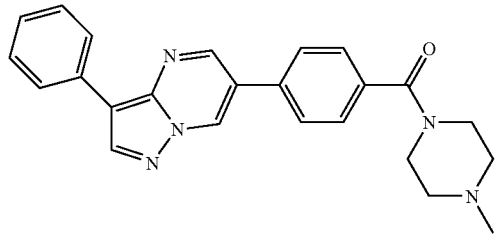

or a pharmaceutically acceptable salt or stereoisomer thereof.

6. The compound according to claim 1 which is 6-(4-{[4-(methylsulfonyl)piperazin-1-yl]methyl}phenyl)-3-phenylpyrazolo[1,5-a]pyrimidine

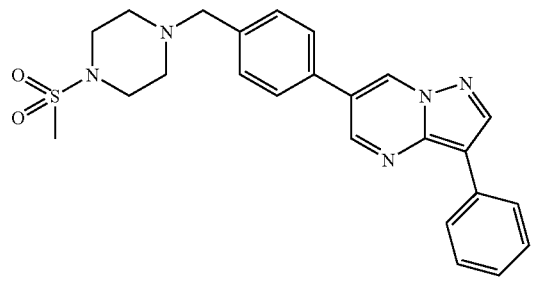

or a pharmaceutically acceptable salt or stereoisomer thereof.

7. A pharmaceutical composition which is comprised of a compound in accordance with claim 1 and a pharmaceutically acceptable carrier.

8. A method of treating cancer in a mammal in need of such treatment which is comprised of administering to said mammal a therapeutically effective amount of a compound of claim 1, wherein the cancer is selected from cancers of the brain, breast carcinoma, genitourinary tract, lymphatic system, stomach, larynx and lung.

* * * * *